(12) United States Patent
Ohyama et al.

(10) Patent No.: US 7,128,742 B2
(45) Date of Patent: Oct. 31, 2006

(54) ELECTRIC OPERATION APPARATUS AND CONTROL METHOD THEREOF

(75) Inventors: Masahide Ohyama, Hino (JP); Kazuya Hijii, Tama (JP); Shinji Hatta, Hachioji (JP); Koji Shimomura, Hachioji (JP); Kenji Harano, Hachioji (JP); Tsuyoshi Hayashida, Sagamihara (JP)

(73) Assignee: Olympus Corporation, Tokyo (JP)

( * ) Notice: Subject to any disclaimer, the term of this patent is extended or adjusted under 35 U.S.C. 154(b) by 175 days.

(21) Appl. No.: 10/615,153

(22) Filed: Jul. 8, 2003

(65) Prior Publication Data

US 2005/0010204 A1 Jan. 13, 2005

(51) Int. Cl.
*A61B 18/18* (2006.01)
(52) U.S. Cl. .......................... 606/41; 607/104; 606/48
(58) Field of Classification Search ............ 606/27–31, 606/41, 42, 45–50; 607/101–105
See application file for complete search history.

(56) References Cited

U.S. PATENT DOCUMENTS

| | | | |
|---|---|---|---|
| 5,697,281 A | 12/1997 | Eggers et al. | |
| 5,891,134 A * | 4/1999 | Goble et al. | 606/27 |
| 6,066,134 A * | 5/2000 | Eggers et al. | 606/32 |
| 6,210,405 B1 * | 4/2001 | Goble et al. | 606/41 |
| 6,616,660 B1 | 9/2003 | Platt | |
| 6,638,274 B1 | 10/2003 | Yamamoto | |
| 2004/0019350 A1 * | 1/2004 | O'Brien et al. | 606/41 |

FOREIGN PATENT DOCUMENTS

| | | |
|---|---|---|
| JP | 09-010223 | 1/1997 |
| JP | 10-286261 | 10/1998 |
| JP | 2000-107196 | 4/2000 |
| JP | 2000-201946 | 7/2000 |
| JP | 2001-145633 | 5/2001 |
| JP | 2001-178740 | 7/2001 |

\* cited by examiner

*Primary Examiner*—Michael Peffley
(74) *Attorney, Agent, or Firm*—Scully, Scott, Murphy & Presser, P.C.

(57) ABSTRACT

An electric operation apparatus includes a high-frequency generating device which generates high-frequency current for treating the body anatomy, an active electrode which supplies to the body anatomy, the high-frequency current generated by the high-frequency generating device, a solution supply device which supplies a conductive solution around the active electrode, a return electrode which returns, via the conductive solution supplied by the solution supply device, the high-frequency current supplied to the body anatomy from the active electrode in the conductive solution, a sensor which detects a conductive state of the high-frequency current that flows between the active electrode and the return electrode, and a control device which determines a state of bubbles generated around the active electrode and which changes an operation mode, based on the conductive state of the high-frequency current detected by the sensor.

8 Claims, 33 Drawing Sheets

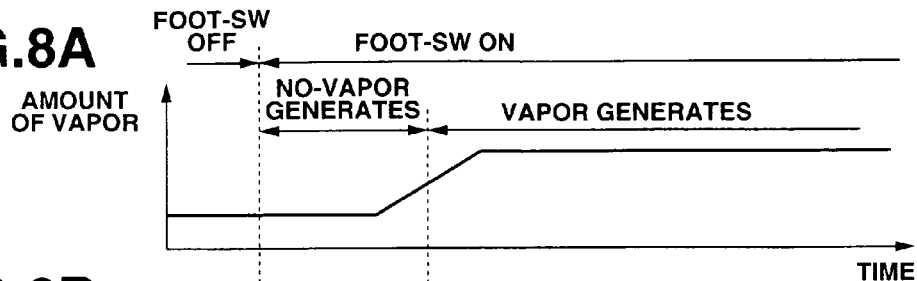
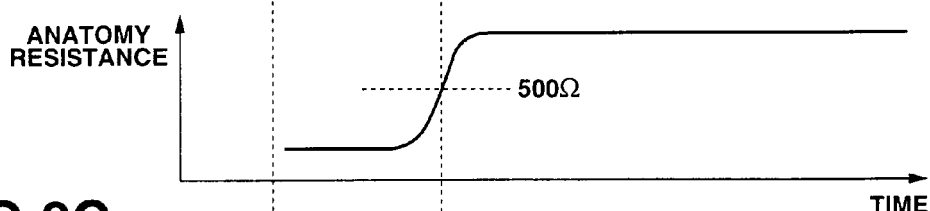
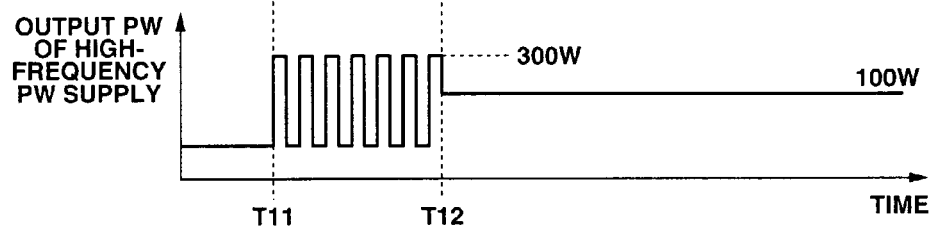
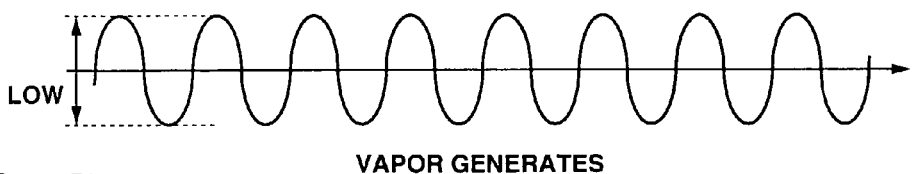
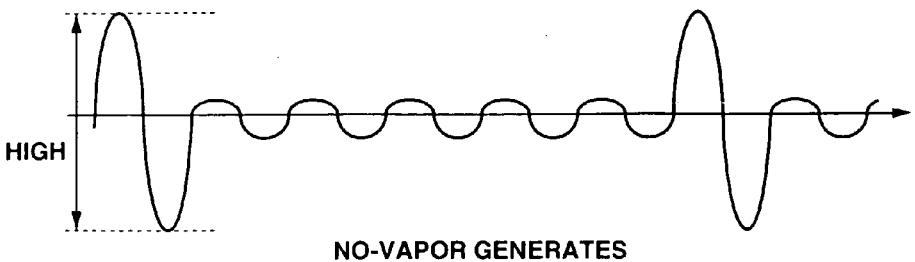

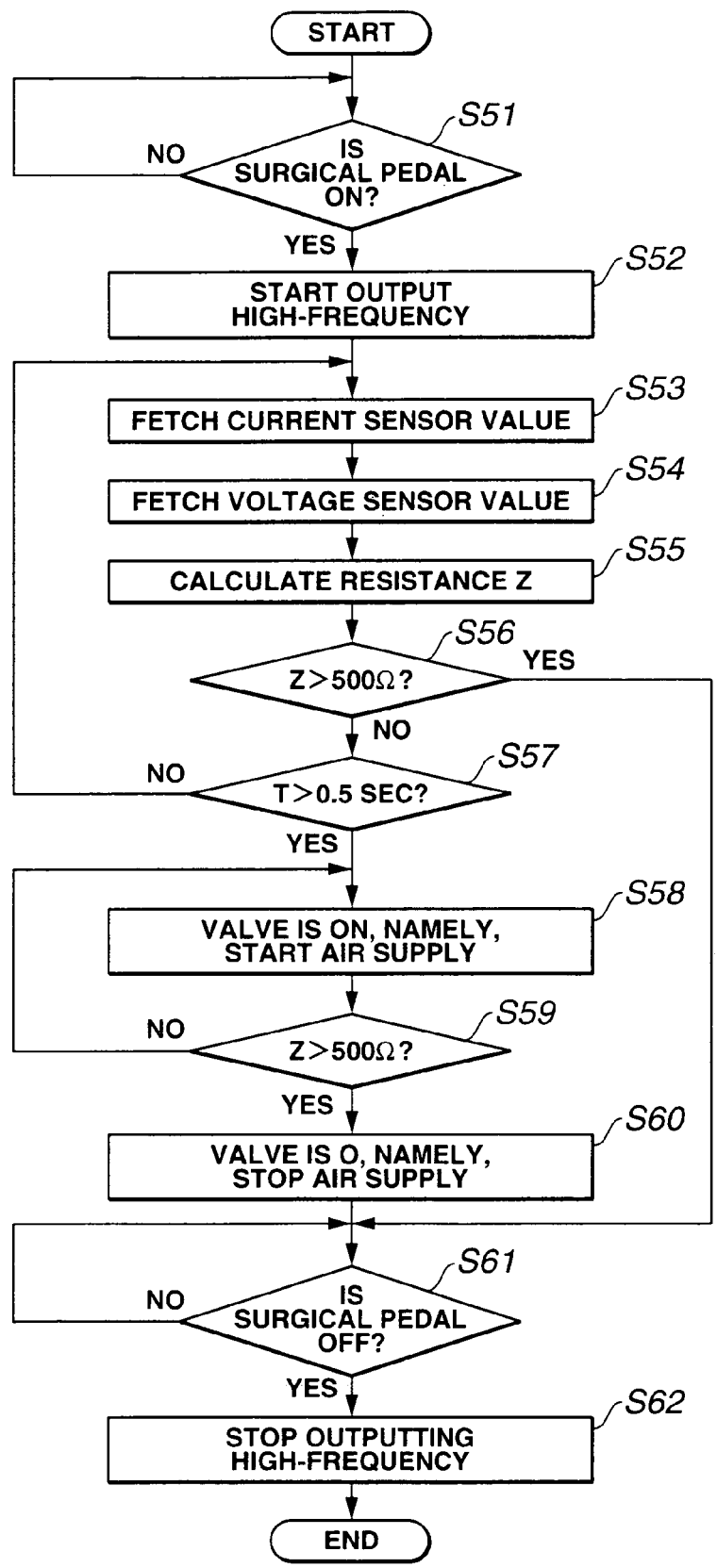

214
(SAW-BLADE-SHAPED)

214
(SPIRAL-SHAPED)

FOOT SW SIGNAL

ELECTRIC OPERATION APPARATUS AND CONTROL METHOD THEREOF

BACKGROUND OF THE INVENTION

1. Field of the Invention

The present invention relates to an electric operation apparatus which is used in a conductive solution and performs electric operation, e.g., resects, transpires, and discharges and coagulates the body anatomy, and a control method thereof.

2. Description of the Related Art

Conventionally, an electric operation apparatus uses a resectoscope, and is used in a conductive solution and performs electric operation, for example, resects, transpires, and discharges and coagulates the body anatomy.

Generally, the resectoscope is used for transurethral resection and transcervical resection, and mainly comprises an optical scope as an endoscope for observation and an electrode unit for cauterizing the anatomy in an elongated and hollow sheath inserted in the coelom.

Upon observation using the resectoscope, a solution is supplied in the coelom through the sheath and the field of view is ensured.

Conventionally, the solution supplied to the coelom is a non-conductive D-sorbitol solution or the like. High-frequency current is collected by a collecting electrode which is extracorporeally arranged via the electrode and the body anatomy.

Here, in the conventional electric operation apparatus, the high-frequency current stimulates the nervus, thereby causing the muscular reflex.

Thus, the conventional electric operation apparatus needs the blocking of high-frequency current against the nervus. The D-sorbitol solution is not supplied in the coelom for a long time and therefore the operation time is limited.

In order to solve the above-mentioned problems, Japanese Unexamined Patent Application Publication No. 2000-201946 discloses a technology which uses physiological saline, as the conductive solution, that is sent to the coelom of the body for a long time, collects the high-frequency current by using the sheath in place of the collecting electrode, and reduces the stimulation of nervus.

Further, U.S. Pat. No. 5,697,281 discloses a technology which applies electric energy to a target position in the body or of the structure on the body by applying a high-frequency voltage between an electrode terminal and a return electrode.

SUMMARY OF THE INVENTION

According to the present invention, an electric operation apparatus includes a high-frequency generating device which generates high-frequency current for treating the body anatomy, an active electrode which supplies to the body anatomy, the high-frequency current generated by the high-frequency generating device, a solution supply device which supplies a conductive solution around the active electrode, a return electrode which returns, via the conductive solution supplied by the solution supply device, the high-frequency current supplied to the body anatomy from the active electrode in the conductive solution, a sensor which detects a conductive state of the high-frequency current that flows between the active electrode and the return electrode, and a control device which determines a state of bubbles generated around the active electrode and which changes an operation mode, based on the conductive state of the high-frequency current detected by the sensor.

Further, according to the present invention, an electric operation apparatus includes a high-frequency generating device which generates high-frequency current for treating the body anatomy, an active electrode which supplies, to the body anatomy, the high-frequency current generated by the high-frequency generating device, a solution supply device which supplies a conductive solution around the active electrode, a return electrode which returns, via the conductive solution supplied by the solution supply device, the high-frequency current supplied to the body anatomy from the active electrode in the conductive solution, a sensor which detects a conductive state of the high-frequency current that flows between the active electrode and the return electrode, and a control device which has a first operation mode for starting the discharge operation by the active electrode and a second operation mode for changing the conductive state of the high-frequency current after the start of discharge operation in the first operation mode, and which determines a state of bubbles generated around the active electrode and which changes the operation mode, based on the conductive state of the high-frequency current detected by the sensor.

Furthermore, according to the present invention, a control method of an electric operation apparatus, includes a solution supply step of supplying a conductive solution around an active electrode by a solution supply device, a first high-frequency output step of outputting high-frequency current in a first operation mode from a high-frequency generating device, when the active electrode is arranged in the conductive solution in the solution supply step, a detecting step of detecting a conductive state of the high-frequency current flowing between the active electrode and a return electrode in the high-frequency output step, a determining step of determining a state of bubbles generated around the active electrode based on a detection result in the detecting step, and a second high-frequency output step of outputting the high-frequency current in a second operation mode based on a determination result in the determining step.

These objects and advantages of the present invention will become further apparent from the following detailed explanation.

BRIEF DESCRIPTION OF THE DRAWINGS

FIG. 8A is a timing chart showing how the amount of vapor changes in the passage of time based on the flowchart shown in FIG. 7;

FIG. 8B is a timing chart showing how the resistance in the anatomy changes in the passage of time based on the flowchart shown in FIG. 7;

FIG. 8C is a timing chart showing how power changes in the passage of time based on the flowchart shown in FIG. 7;

FIG. 9A is an explanatory diagram showing a waveform of high-frequency current upon generating vapor based on the flowchart shown in FIG. 7;

FIG. 9B is an explanatory diagram showing a waveform of high-frequency current upon generating no vapor based on the flowchart shown in FIG. 7;

FIG. 30 is a flowchart showing the control operation of a control circuit according to the fifth embodiment;

DESCRIPTION OF THE PREFERRED EMBODIMENTS

Hereinbelow, a description is given of embodiments of the present invention with reference to the drawings.

(First Embodiment)

FIGS. 1 to 6C are diagrams according to a first embodiment of the present invention.

Figure 1:
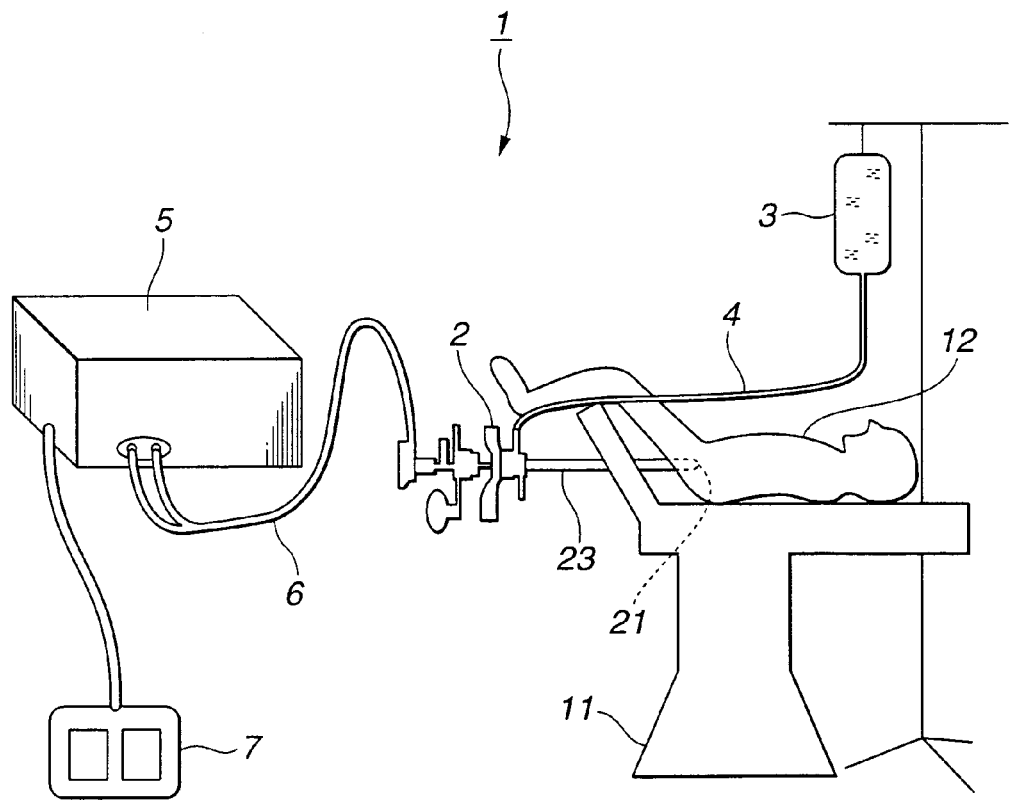
FIG. 1 is a diagram showing the entire structure of an electric operation apparatus according to a first embodiment of the present invention.

Referring to FIG. 1, an electric operation apparatus 1 comprises a resectoscope 2, a pack of a physiological saline (hereinafter, referred to as a physiological saline pack) 3, and a high-frequency power supply 5. A patient 12 is laid on an operation table 11.

An edge portion 21 of the resectoscope 2 is inserted in the urethra of the patient 12. An electrode 22 shown in FIG. 3 arranged to the edge portion 21 reaches the periphery of the treated anatomy.

The high-frequency power supply 5 is connected to a coating tube 23 of the resectoscope 2 and the electrode 22 which is attached to the edge portion 21 of the resectoscope 2 via an electrode cable 6.

The physiological saline pack 3 is connected to the resectoscope 2 via a solution supply tube 4. In this case, the resectoscope 2 has a tube 26 therein shown in FIG. 4. The solution supply tube 4 is connected to a base end side of the tube 26.

A foot switch 7 for controlling the on/off operation of a high-frequency output is connected to the high-frequency power supply 5.

FIGS. 10 to 13 show a state near the electrode 22 arranged to the edge of the resectoscope 2 which is usually used.

Figure 10:
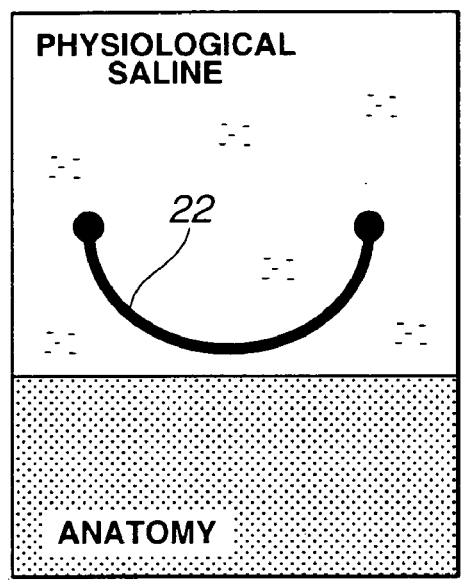
FIG. 10 is a first diagram for explaining the operation of the periphery of an electrode of the resectoscope which is normally used.
Figure 11:
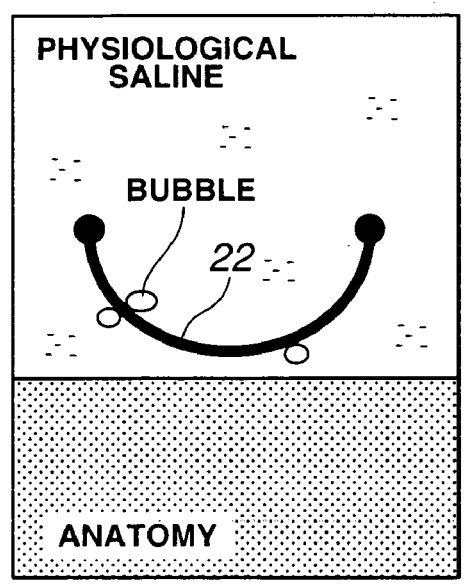
FIG. 11 is a second diagram for explaining the operation of the periphery of the electrode of the resectoscope which is normally used.
Figure 12:
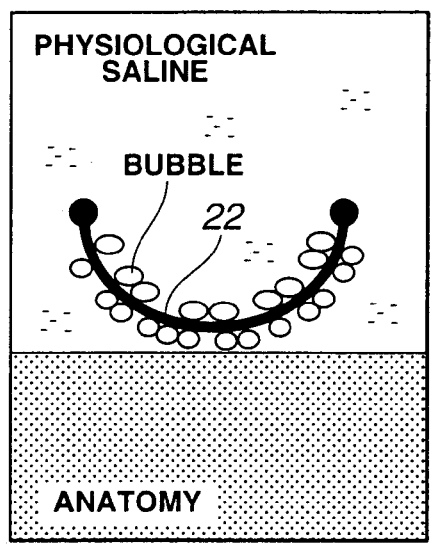
FIG. 12 is a third diagram for explaining the operation of the periphery of the electrode of the resectoscope which is normally used.
Figure 13:
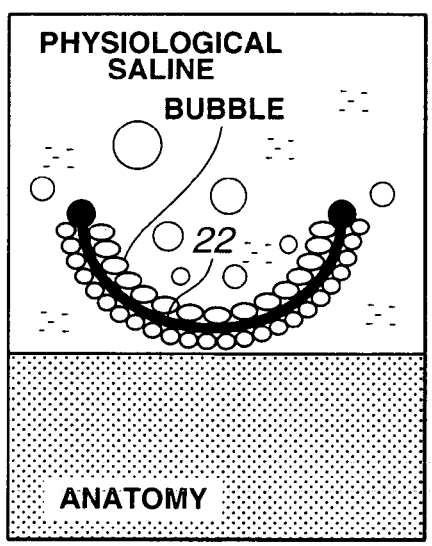
FIG. 13 is a fourth diagram for explaining the operation of the periphery of the electrode of the resectoscope which is normally used.

The high-frequency current starts to be supplied to the electrode 22 (FIG. 10). Then, the generated energy heats the physiological saline near the electrode 22 and the bubbles start to be generated (FIG. 11). Further, the energy is continuously supplied to the electrode 22 and then the amount of bubbles is increased, thus covering the entire periphery of the electrode 22 (FIG. 12). When the entire periphery of the electrode 22 is covered with the bubbles (FIG. 13), the electric resistance among the electrode 22, the physiological saline, and the body anatomy sharply increases and a high voltage is generated. Therefore, the discharge operation starts. Heat generated by the discharge operation enables the body anatomy to be resected, be transpired, and be discharged and coagulated.

However, the heating of physiological saline and the generation of bubbles need high power. Thus, an expensive high-frequency power supply for outputting high power is necessary to resect, transpire, and discharge and coagulate the body anatomy in the conductive solution.

According to the first embodiment, the high-frequency power supply 5 detects the evaporation of the conductive solution and reduces power of a high-frequency output upon detecting the evaporation in order to measure a high-frequency voltage and the high-frequency current, to calculate the impedance between the electrode 22 arranged to the edge portion 21 and the coating tube 23, and to determine a state of bubbles near the electrode 22.

Figure 2:
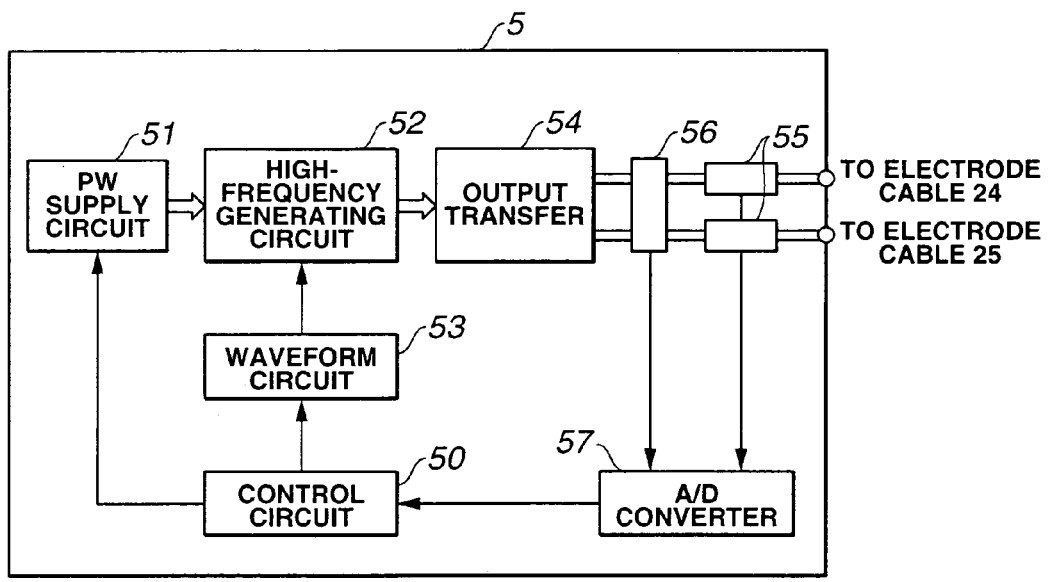
FIG. 2 is a circuitry block diagram showing a high-frequency power supply shown in FIG. 1.

Referring to FIG. 2, the high-frequency power supply 5 comprises: a control circuit 50; a power supply circuit 51; a high-frequency generating circuit 52; a waveform circuit 53; an output transfer 54; a current sensor 55; a voltage sensor 56; and an A/D converter 57.

The power supply circuit 51 outputs DC current. The high-frequency generating circuit 52 converts the DC current from the power supply circuit 51 into the high-frequency current. The waveform circuit 53 instructs a waveform of the high-frequency current to the high-frequency generating circuit 52 under the control operation of the control circuit 50.

The output transfer 54 outputs the high-frequency current from the high-frequency generating circuit 52 to electrode cables 24 and 25 of the resectoscope 2. The current sensor 55 detects output current outputted from the output transfer 54. The voltage sensor 56 detects an output voltage outputted from the output transfer 54. The A/D converter 57 converts signals from the current sensor 55 and the voltage sensor 56 into digital signals. The control circuit 50 controls the power supply circuit 51 and the waveform circuit 53 based on the signal from the foot switch 7 and the digital data from the A/D converter 57.

Figure 3:
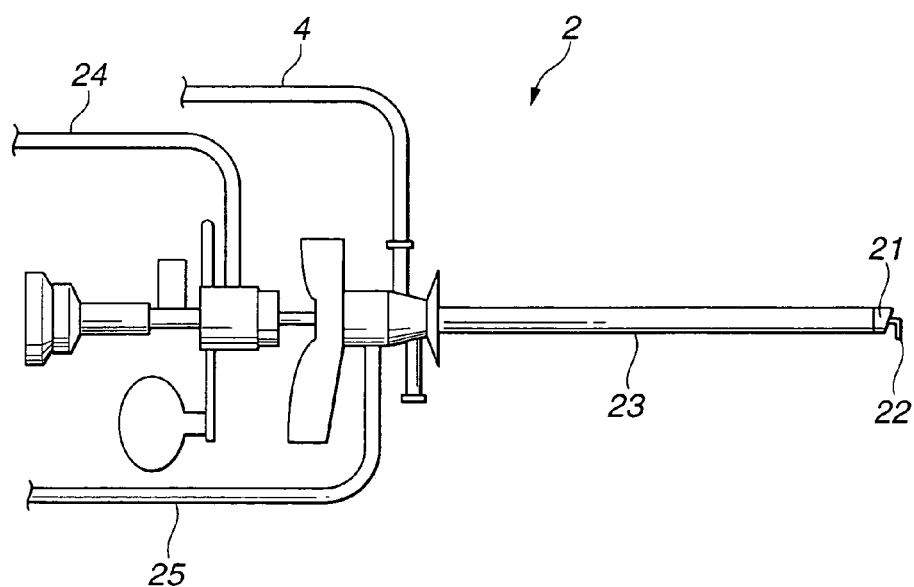
FIG. 3 is an external view showing a resectoscope shown in FIG. 1.

Referring to FIG. 3, the resectoscope 2 comprises: the electrode cable 24 conductive to the electrode 22 of the edge portion 21 and the electrode cable 25 conductive to the coating tube 23.

Figure 4:
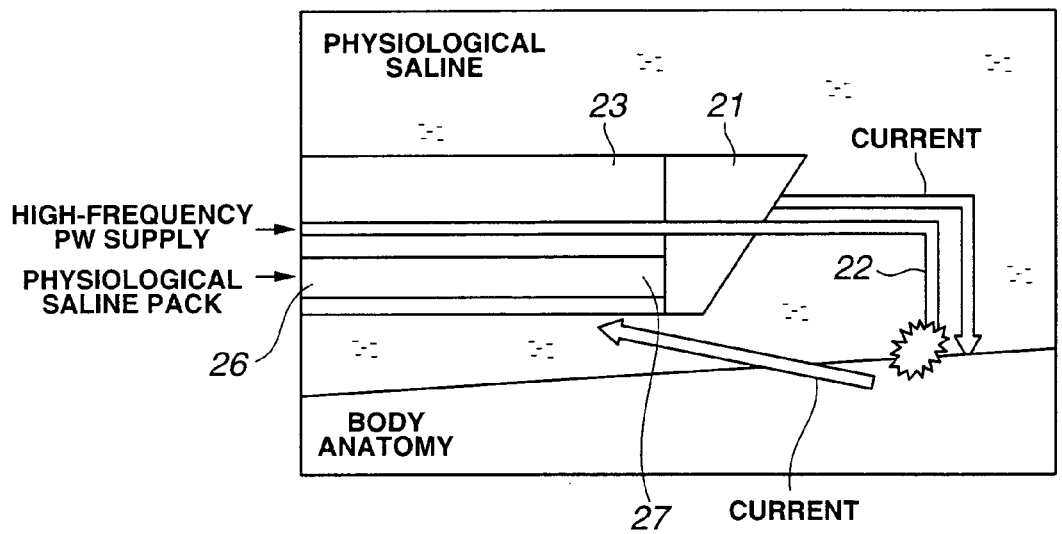
FIG. 4 is an enlarged view showing an edge of the resectoscope shown in FIG. 3.

Next, a description is given of the edge portion 21 of the resectoscope 2 with reference to FIG. 4.

Referring to FIG. 4, the electrode 22 is exposed from the edge portion 21 of the resectoscope 2. The electrode 22 is bent to be L-shaped and easily comes into contact with the body anatomy.

The edge portion 21 has an air and solution supply vent 27 which is arranged on the edge side of the tube 26. Thus, the physiological saline from the physiological saline pack 3 is transmitted from the air and solution supply vent 27.

The high-frequency current from the high-frequency power supply 5 flows to the body anatomy from the electrode 22 and is collected to the coating tube 23.

A description is given of the operation with the above-mentioned structure according to the first embodiment.

Figure 5:
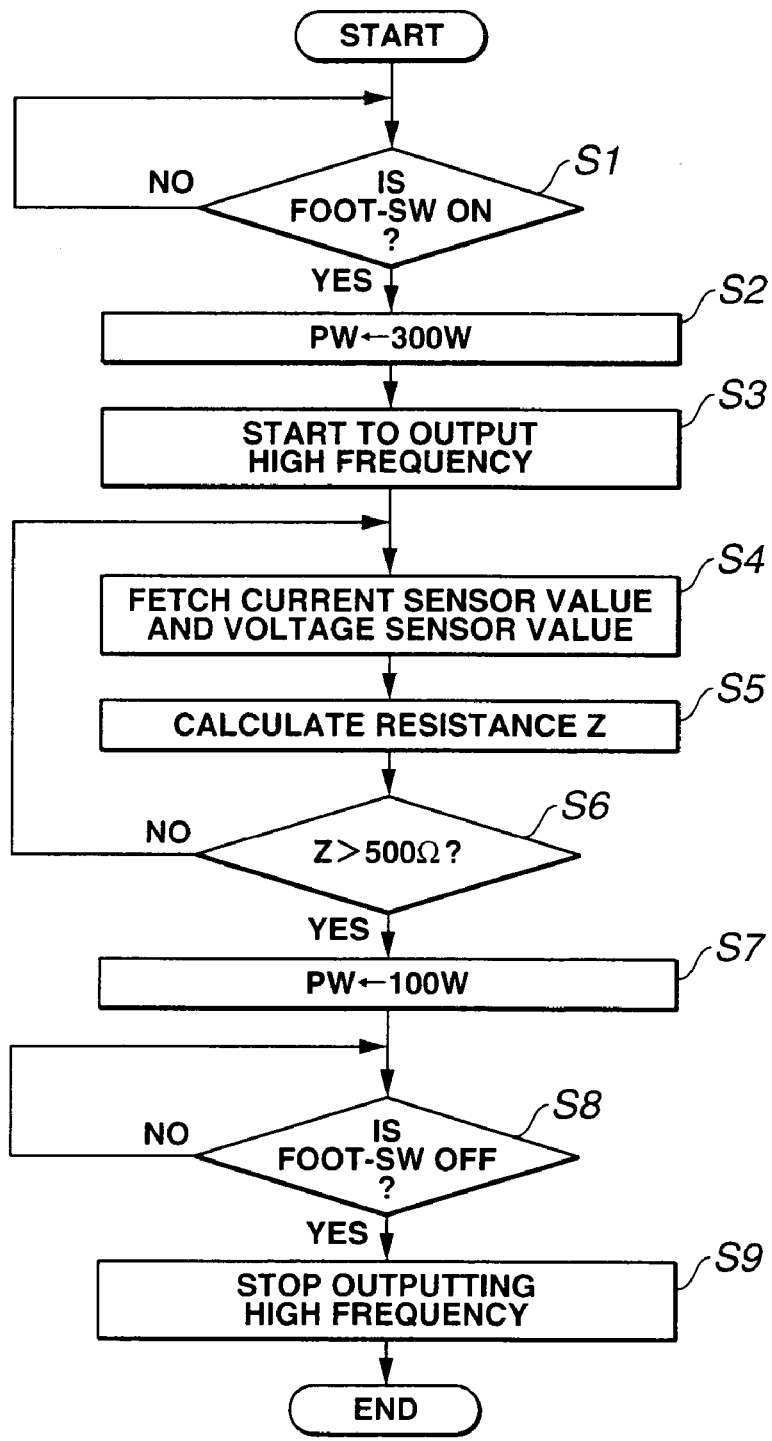
FIG. 5 is a flowchart showing the control operation of a control circuit according to the first embodiment.

The operation of the control circuit 50 is performed in accordance with a flowchart shown in FIG. 5.

Referring to FIG. 5, the foot switch 7 is pressed in step S1. Then, the control circuit 50 sets the power outputted by the high-frequency power supply 5 to 300 W in step S2. The control circuit 50 allows the high-frequency power supply 5 to output a high frequency in step S3.

Figure 6A:
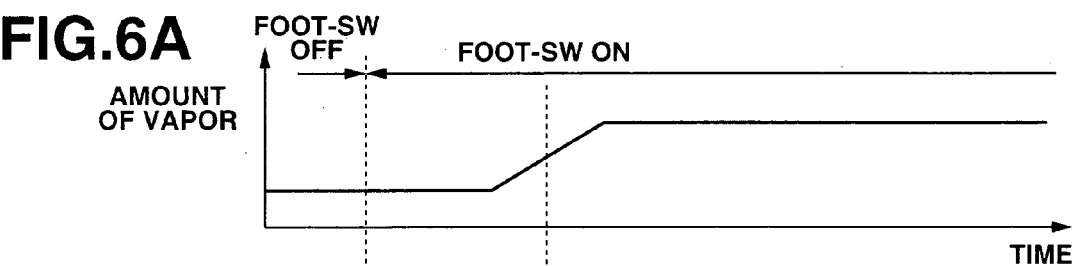
FIG. 6A is a timing chart showing how the amount of vapor changes in the passage of time based on the flowchart shown in FIG. 5.
Figure 6B:
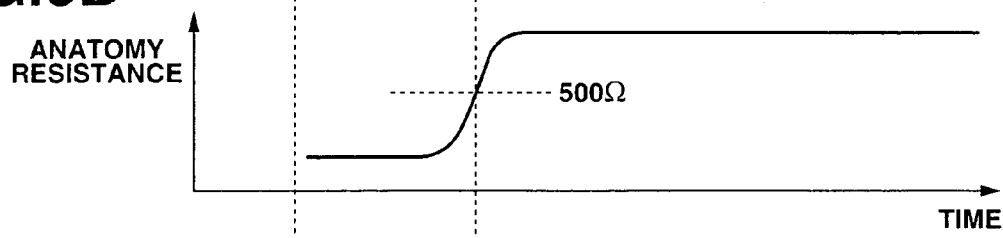
FIG. 6B is a timing chart showing how the resistance in the anatomy changes in the passage of time based on the flowchart shown in FIG. 5.
Figure 6C:
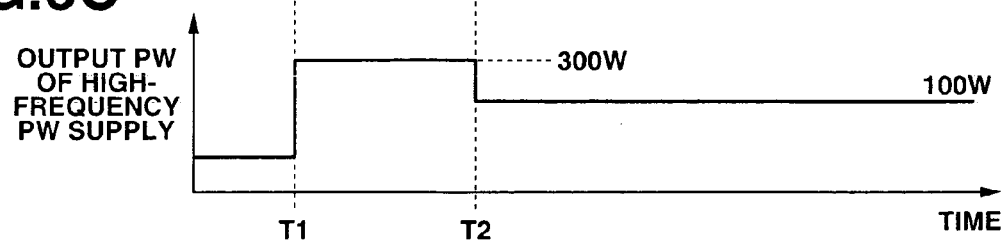
FIG. 6C is a timing chart showing how power changes in the passage of time based on the flowchart shown in FIG. 5.

An interval from timings T1 to T2 shown in FIGS. 6A to 6C corresponds to steps subsequent to step S3 whereupon power of 300 W is outputted.

Next, in step S4, the control circuit 50 fetches a current value of the current sensor 55 via the A/D converter 57 and further fetches a voltage value of the voltage sensor 56 via the A/D converter 57.

After that, in step S5, the control circuit 50 calculates a resistance Z between the electrode 22 and the coating tube 23 by dividing the voltage value fetched in the circuit by the current value, and shifts to processing in step S6.

In step S6, the control circuit 50 repeats the similar processing in step S4 and steps subsequent thereto, when the resistance Z is less than 500 Ω. The measurement and determination are repeated at the interval from the timings T1 to T2 shown in FIGS. 6A to 6C.

The high frequency starts to be outputted to the high-frequency power supply 5 and the high-frequency current from the high-frequency power supply 5 flows to the body anatomy from the electrode 22. The high-frequency current is collected in the coating tube 23 and then the physiological saline starts to be evaporated.

The vapor covers the periphery of the electrode 22 and then the resistance Z gradually rises. The bubbles cover the entire periphery of the electrode 22 and the discharge operation starts and then the resistance Z is higher than 500 Ω. The above-mentioned phenomenon is caused at the timing T2 shown in FIGS. 6A to 6C.

In step S6, the control circuit 50 determines that the entire periphery of the electrode 22 is covered with the bubbles and the discharge operation has already been caused when the resistance Z is higher than 500 Ω, and the processing sequence shifts to step S7.

Here, the high-frequency power supply 5 according to the first embodiment is a small power supply which does not have sufficient capacity for always outputting power of 300 W.

However, the discharge operation is caused once and then even small power evaporates the physiological saline. Thus, the large output of 300 W is not necessary.

Therefore, in step S7, the control circuit 50 changes the power setting to 100 W and outputs the high frequency.

A timing for changing the power setting in step S7 corresponds to the timing T2 shown in FIGS. 6A to 6C. In the halfway of the timing T2, the power setting is changed to 100 W and, consequently, the small power supply enables the discharge operation in the physiological saline.

In step S8, the foot is detached from the foot switch 7. Then, in step S9, the control circuit 50 controls the power supply circuit 51 or the high-frequency generating circuit 52 and stops the high-frequency output.

A detailed description is given of a relationship between the above operation and time with reference to FIGS. 6A to 6C.

Referring to FIGS. 6A to 6C, when the foot switch 7 is off before the timing T1, the output of the high-frequency current is off from the high-frequency power supply 5 to the electrode 22 and the resistance in the anatomy is not detected.

When the foot switch 7 is turned on at the timing T1, the bubbles are generated from the electrode 22. However, just after turning on the foot switch 7, a small amount of bubbles is generated in the electrode 22, and the resistance Z in the anatomy is lower than 500 Ω. Therefore, the control circuit 50 sets the power outputted by the high-frequency power supply 5 to 300 W.

After turning on an on/off pedal of the foot switch 7 and passing some time, the bubbles cover the electrode 22 and the resistance Z increases. When the resistance Z is 500 Ω, the discharge operation has already started and the control circuit 50 changes the setting of power to 100 W and outputs the high frequency.

With the above-described structure and operation, the high-frequency power supply 5 becomes a high-frequency generating device which generates high-frequency current.

The electrode 22 is an active electrode for transmitting the high-frequency current to the body anatomy, arranged in the conductive solution.

The coating tube 23 is a return electrode which collects the high-frequency current that flows to the body anatomy from the active electrode.

The physiological saline pack 3 and the solution supply tube 4 are solution supply devices which supply the conductive solution near the electrode.

The current sensor 55, the voltage sensor 56, the A/D converter 57, and the control circuit 50 are vapor detecting portions which detect the vapor of the conductive solution near the active electrode.

The vapor detecting portions measure the high-frequency voltage and the high-frequency current, calculate the impedance between the active electrode and the return electrode based on the measurement result, and detect the vapor of the conductive solution.

The control circuit 50 is a control device which controls the high-frequency generating device based on information from the vapor detecting portions. Further, the control circuit 50 is a control device which changes the power of the high-frequency output.

As described above, according to the first embodiment, the power of the high-frequency output from the high-frequency power supply 5 is high until the vapor of the conductive solution is detected near the electrode 22. Upon detecting the vapor of the conductive solution, the power of the high-frequency output from the high-frequency power supply 5 is reduced. Thus, the high-frequency power supply 5 does not need enough capacity to always generate high output, and uses the small power supply. The manufacturing costs of the electric operation apparatus are reduced and the power consumption is saved.

(Second Embodiment)

FIGS. 7 to 9B are diagrams according to a second embodiment.

According to the second embodiment, the structure is almost the same as that according to the first embodiment. Therefore, only different points are described. Portions not shown in FIGS. 7 to 9B are described with reference to FIGS. 1 to 4.

Only the control circuit 50 and the waveform circuit 53 according to the second embodiment are different from those shown in FIG. 2. Other structures are the same as those according to the first embodiment.

A description is given of the operation with the above structure according to the second embodiment.

Figure 7:
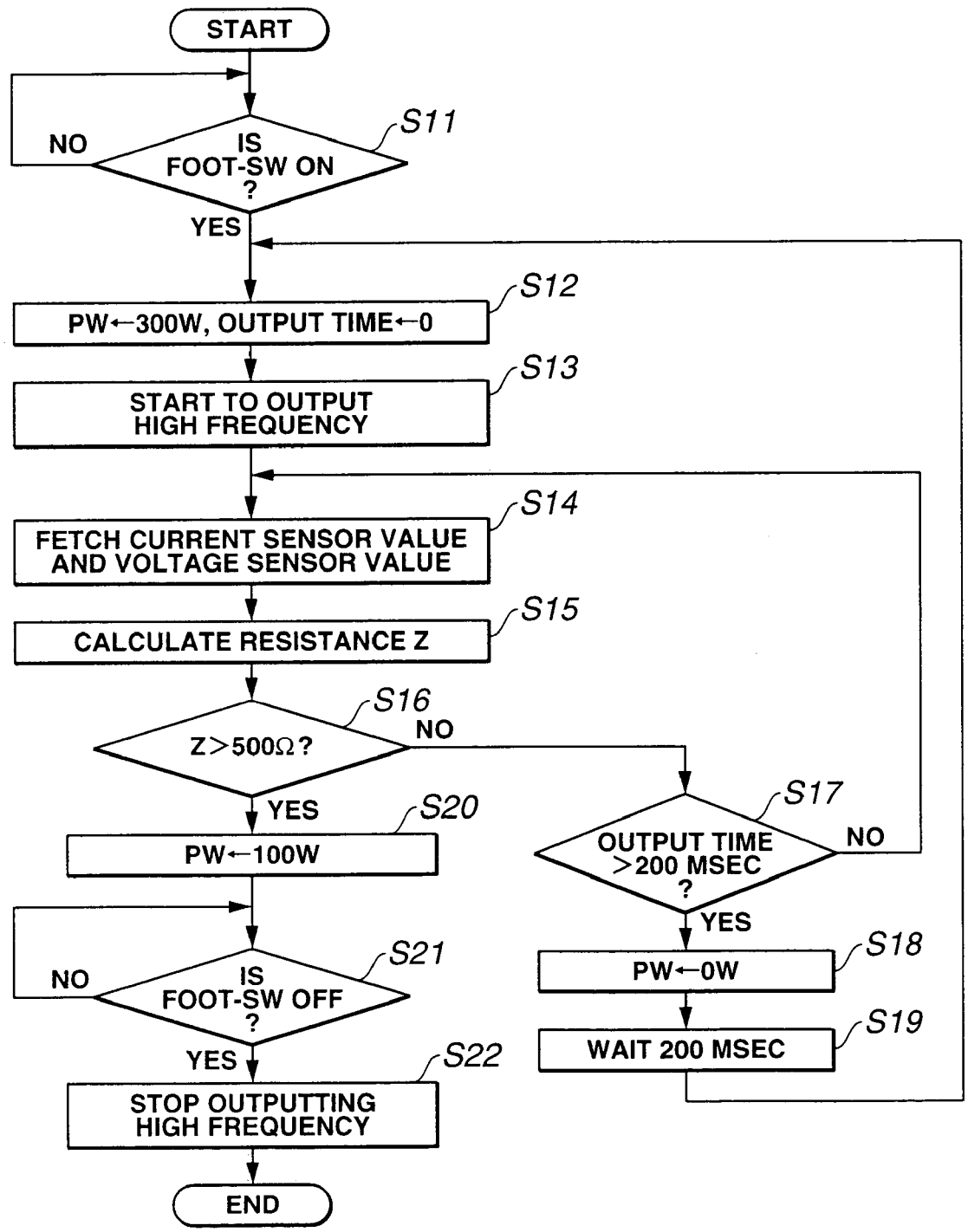
FIG. 7 is a flowchart showing the control operation of a control circuit according to a second embodiment.

The operation of the control circuit 50 is shown in a flowchart shown in FIG. 7.

Referring to FIG. 7, in step S11, the foot switch 7 is pressed. In step S12, the control circuit 50 sets the power outputted from the high-frequency power supply 5 to 300 W, and sets output time to zero. In step S13, the control circuit 50 enables the high-frequency power supply 5 to output the high frequency.

Next, in step S14, the control circuit 50 fetches a current value of the current sensor 55 via the A/D converter 57, and further fetches a voltage value of the voltage sensor 56 via the A/D converter 57.

After that, in step S15, the control circuit 50 divides the voltage value fetched therein by the current value, thereby calculating the resistance Z between the electrode 22 and the coating tube 23. Then, the processing sequence shifts to step S16.

In step S16, the control circuit 50 determines whether or not the resistance Z is over 500 Ω. When the resistance Z is less than 500 Ω, the processing sequence shifts to step S17. When the resistance Z is more than 500 Ω, the processing sequence shifts to step S20.

In step S17, the control circuit 50 determines whether or not the output time is over 200 msec. When the output time is shorter than 200 msec, the processing sequence returns to step S14. When the output time is longer than 200 msec, the processing sequence shifts to step S18.

That is, when the resistance Z is, e.g., less than 500 Ω in step S16 and when the output time is shorter than 200 msec in step S17, the processing of steps S14, S15, S16, and S17 is repeated.

When the output time is longer than 200 msec in step S17, the control circuit 50 stops the high-frequency output in step S18. In step S19, the control circuit 50 waits for 200 msec. Thereafter, the similar processing from step S12 is repeated.

At an interval from timings T11 to T12 shown in FIGS. 8A to 8C, the high-frequency output and the stop thereof in steps S12 to S19 are repeated. The waveform of the high-frequency output at the interval has a large peak value as shown in FIG. 9B.

The physiological saline starts to evaporate and the periphery of the electrode 22 is covered with the vapor. Then, the resistance Z gradually increases. The entire periphery of the electrode 22 is covered with the bubbles and the discharge operation starts. Then, the resistance Z is higher than 500 Ω.

At the timing T12 shown in FIGS. 8A to 8C, the above phenomenon is caused. The discharge operation starts and, then, the physiological saline evaporates by even low power. Thus, the output with the high power is not necessary. In step S20, the control circuit 50 changes the power setting to 100 W and outputs the high frequency. The timing for changing the power setting in step S20 corresponds to the timing T12 shown in FIGS. 8A to 8C. In this case, the waveform of the high-frequency output has a small peak value as shown in FIG. 9A. As mentioned above, in the halfway, the power setting is changed to 100 W and, therefore, the discharge operation is possible in the physiological saline by using the small power supply.

In step S21, the foot is detached from the foot switch 7. Then, in step S22, the control circuit 50 controls the power supply circuit 51 or the high-frequency generating circuit 52 to stop the high-frequency output.

With the above-mentioned structure and operations, the control circuit 50 controls the high-frequency power supply 5 so that the peak of the high-frequency power is high before detecting the vapor of the conductive solution and the peak of the high-frequency power after detecting the vapor is low.

Further, the control circuit 50 controls the high-frequency power supply 5 so as to repeat processing in steps S12 to S17 for outputting first high-frequency power and processing in steps S18 and S19 for outputting second high-frequency power lower than the first high-frequency power including zero power before detecting the vapor of the conductive solution.

Furthermore, the control circuit 50 controls the high-frequency power supply 5 so as to increase a crest factor of the high-frequency current with a waveform of the high peak-value as shown in FIG. 9B before detecting the vapor of the conductive solution.

In addition, the control circuit 50 controls the high-frequency power supply 5 so as to reduce the crest factor of the high-frequency current with a waveform of the low peak-value as shown in FIG. 9A after detecting the vapor of the conductive solution.

According to the second embodiment, in addition to the advantages according to the first embodiment, the output of high power and the stop thereof are repeated until the physiological saline evaporates, and further the waveform having the high peak is used. Therefore, the high-frequency power supply with the small capacity enables the evaporation of the conductive solution and the anatomy is resected, is transpired, and is discharged and coagulated in the conductive solution.

According to the first and second embodiments, referring to FIGS. 1 to 9B, the vapor detecting portions for detecting the vapor of the conductive solution near the active electrode comprise the current sensor 55, the voltage sensor 56, and the A/D converter 57 which measure the high-frequency voltage and the high-frequency current. However, the present invention is not limited to this and the vapor detecting unit can comprise only a measuring portion which measures one of the high-frequency voltage and the high-frequency current.

Further, according to the first and second embodiments, referring to FIGS. 1 to 9B, the electric operation apparatus is applied to the resectoscope which is formed by integrating the optical scope and the electrode unit for cauterizing the body anatomy. However, the present invention can be applied to an electric operation apparatus which is formed by arranging the electric unit for cauterizing the body anatomy independently of the endoscope of the optical scope.

(Third Embodiment)

FIGS. 14 to 19C are diagrams according to a third embodiment.

The structure according to the third embodiment is almost the same as that according to the first embodiment, and only different points are described.

Figure 14:
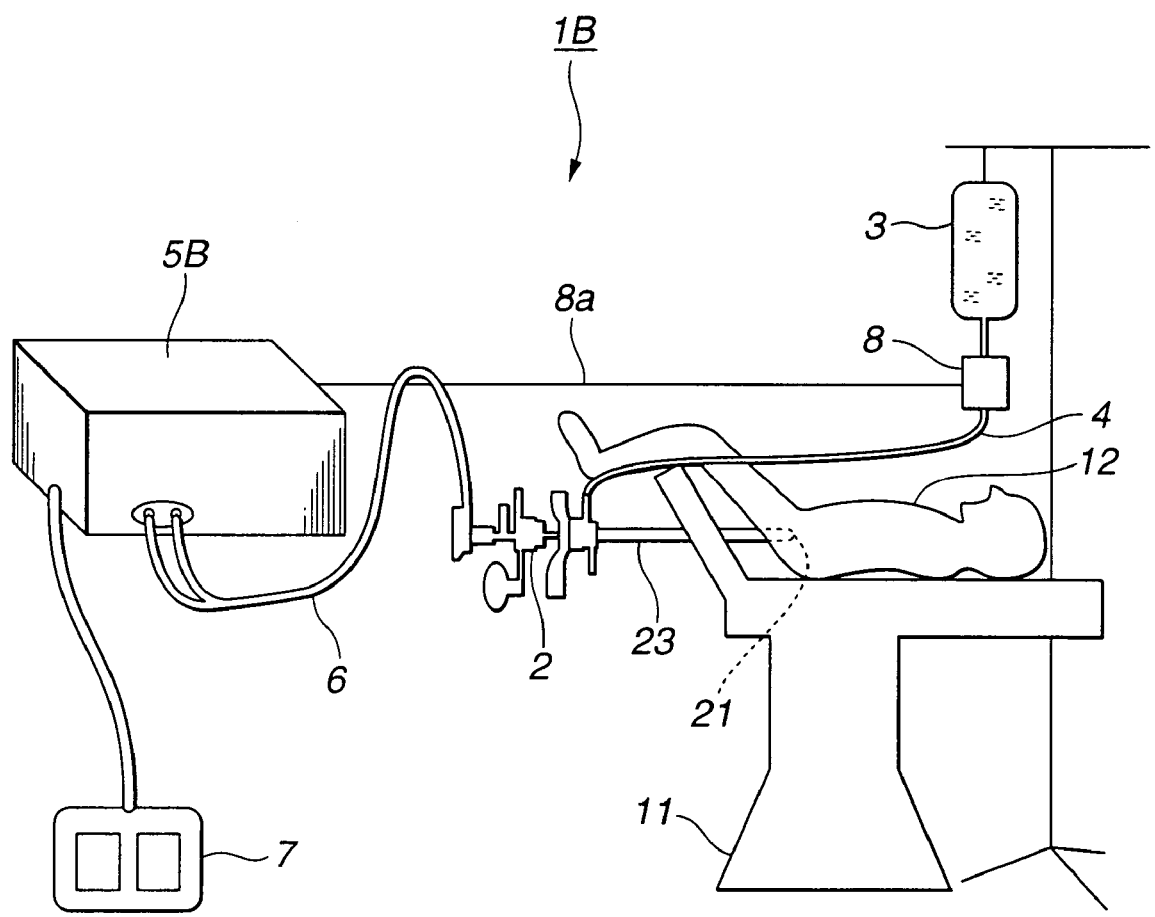
FIG. 14 is a diagram showing the entire structure of an electric operation apparatus according to a third embodiment.

Referring to FIG. 14, an electric operation apparatus 1B according to the third embodiment comprises a pinch valve 8.

The pinch valve 8 is attached to the solution supply tube 4. Further, a high-frequency power supply 5B supplies power to the pinch valve 8 via a pinch valve cable 8a.

The high-frequency power supply 5B starts the output and is covered with bubbles of the electrode 22. Further, the high-frequency power supply 5B controls the pinch valve 8 until the discharge operation starts to stop the solution supply via the solution supply tube 4.

Figure 15:
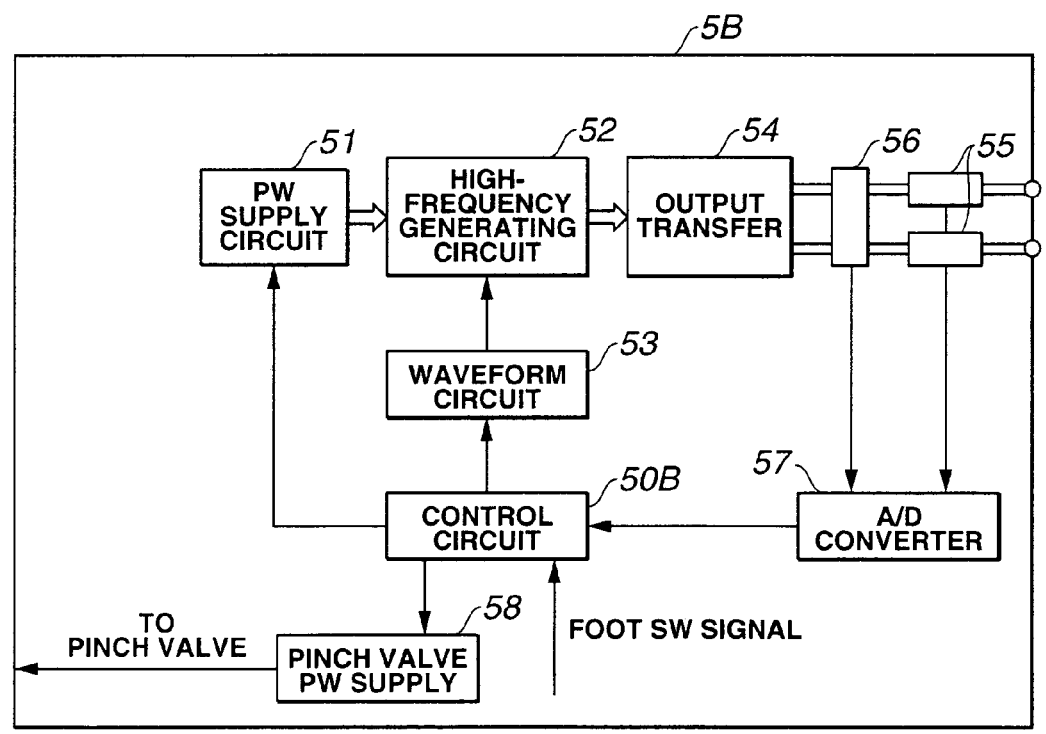
FIG. 15 is a circuitry block diagram showing a high-frequency power supply shown in FIG. 14.

Referring to FIG. 15, the high-frequency power supply 5B has a pinch valve power supply 58.

A control circuit 50B controls the power supply circuit 51 and the waveform circuit 53 based on the digital data from the A/D converter 57 and the signal from the foot switch 7. Further, the control circuit 50B controls the pinch valve power supply 58 which supplies power to the pinch valve 8.

The pinch valve 8 will be described with reference to FIGS. 16 and 17.

Figure 16:
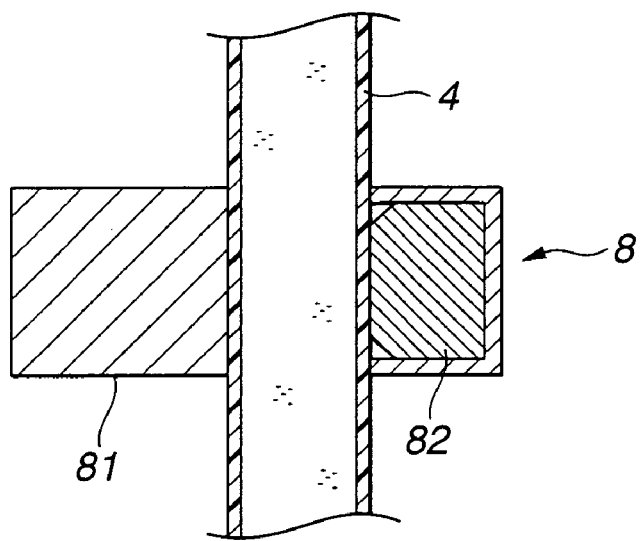
FIG. 16 is a side view when the supply of solution in a pinch valve shown in FIG. 14 is not stopped.
Figure 17:
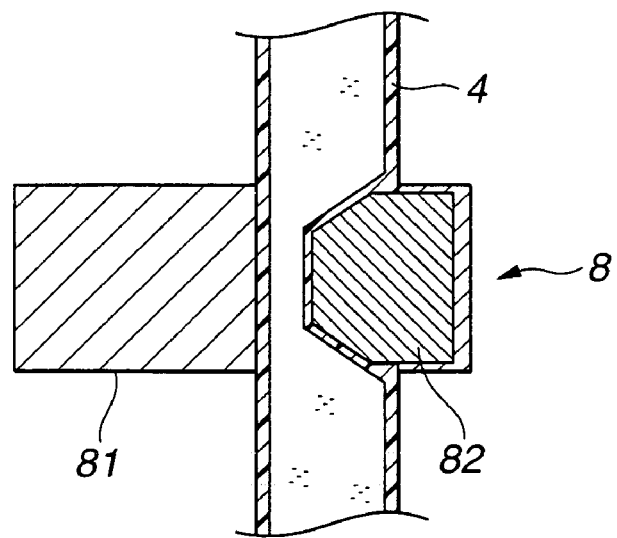
FIG. 17 is a side view when the supply of solution in the pinch valve shown in FIG. 14 is stopped.

Referring to FIGS. 16 and 17, the pinch valve 8 comprises a solution supply tube supporting portion 81 and a solution supply tube pressing portion 82.

The solution supply tube supporting portion 81 supports the solution supply tube 4 while the solution supply tube 4 is inserted therein.

Referring to FIG. 16, when the pinch valve 8 does not stop the solution supply, the solution supply tube pressing portion 82 does not press the solution supply tube 4. Referring to FIG. 17, when the pinch valve 8 stops the solution supply, the solution supply tube pressing portion 82 presses the solution supply tube 4.

The operation with the above structure will be described according to the third embodiment.

Figure 18:
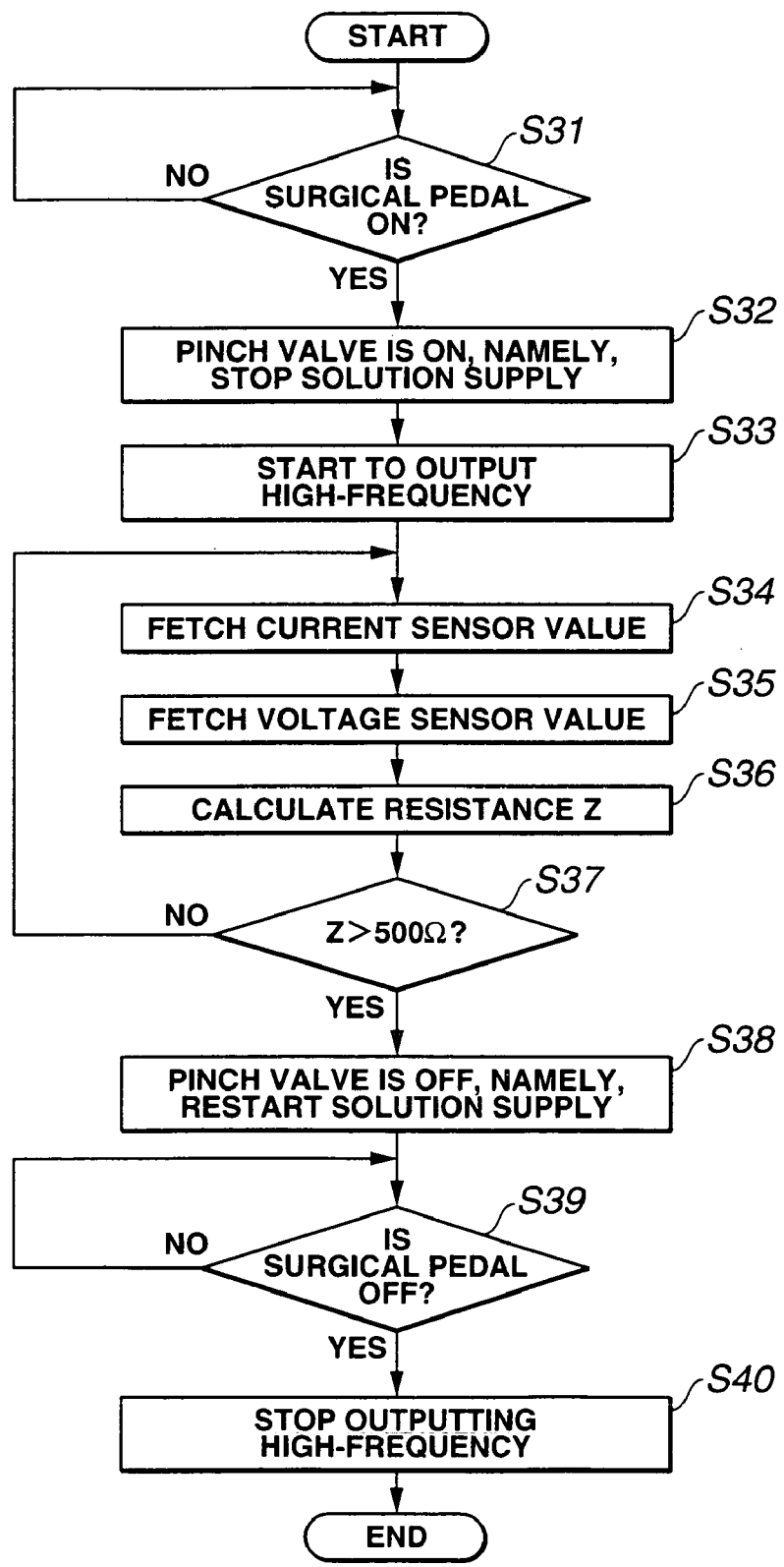
FIG. 18 is a flowchart showing the control operation of a control circuit according to the third embodiment.
Figure 19:
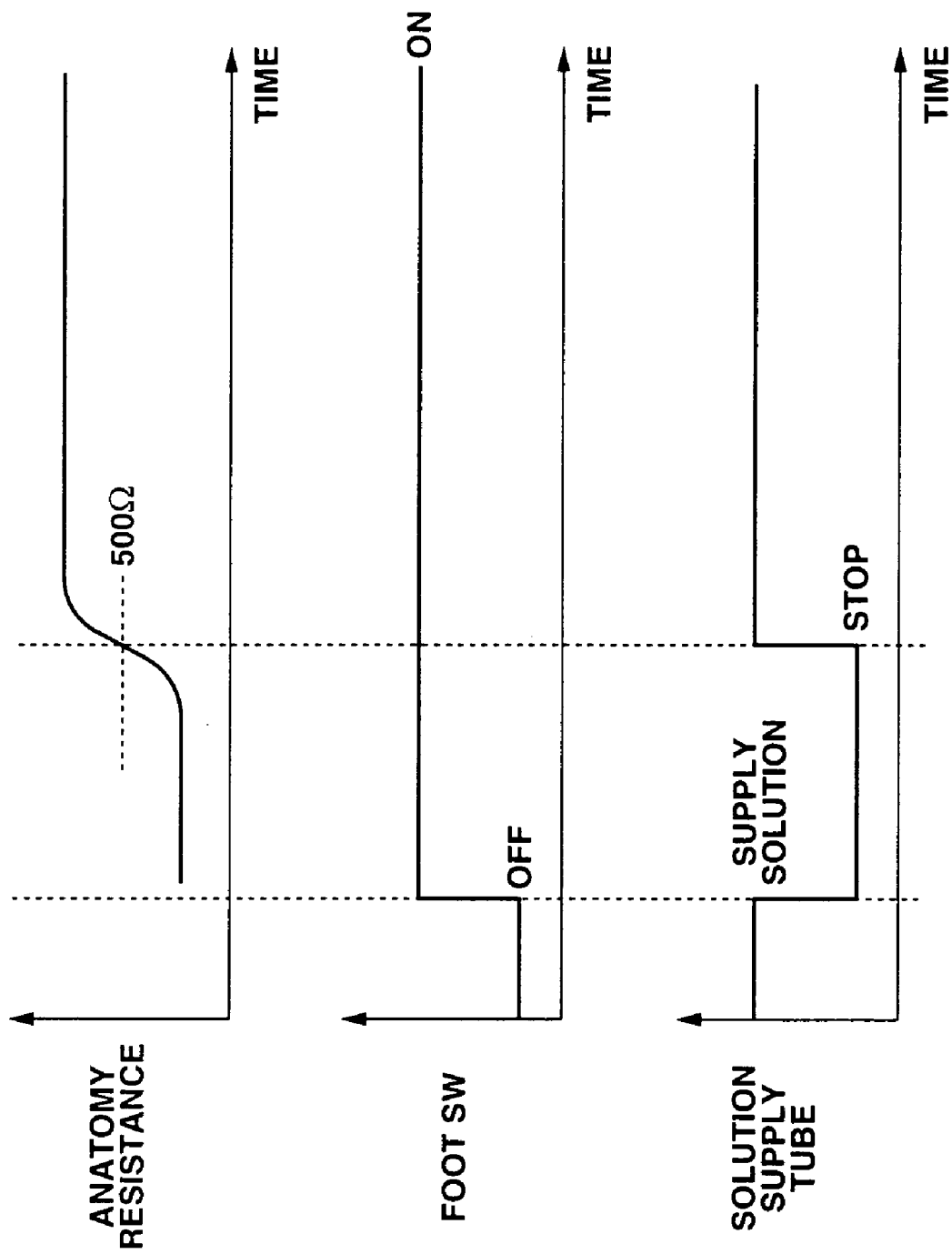
FIG. 19A is a timing chart showing how the resistance in the anatomy changes in the passage of time based on the flowchart shown in FIG. 18.
FIG. 19B is a timing chart showing the operation of a foot switch based on the flowchart shown in FIG. 18.
FIG. 19C is a timing chart showing a state of supplying a solution via a solution supply tube in accordance with the operation of a pinch valve based on the flowchart shown in FIG. 18.

FIG. 18 is a flowchart showing the operation of the control circuit 50B.

Referring to FIG. 18, in step S31, an on/off pedal of the foot switch 7 is pressed. In step S32, the control circuit 50B controls the pinch valve power supply 58 so that power is supplied to the pinch valve 8 and the solution supply tube 4 temporarily stops the solution supply. In step S33, the control circuit 50B controls the high-frequency generating circuit 52 to output the high frequency. In this case, the solution supply stops and therefore the physiological saline heated by the high-frequency current remains near the electrode 22 and the bubbles are easily generated. The generated bubbles are not scattered by the solution supply.

After that, in steps S34 and S35, the control circuit 50B fetches the current value of the current sensor 55 and the voltage value of the voltage sensor 56 via the A/D converter 57.

Further, in step S36, the control circuit 50B divides the voltage value fetched therein by the current value, thereby calculating the resistance Z between the electrode 22 and the coating tube 23.

In step S37, when the resistance Z is lower than 500 Ω, the processing sequence returns to step S34 whereupon the control circuit 50B repeats the similar processing.

In step S37, when the resistance Z is higher than 500 Ω, the entire periphery of the electrode 22 is covered with the bubbles and the discharge operation has already been started. Thus, the stop operation of solution supply is not necessary. Therefore, the control circuit 50B shifts to processing in step S38.

In step S38, the control circuit 50B shuts off the power to the pinch valve 8, and restarts the solution supply.

In step S39, the on/off pedal of the foot switch 7 is off. Then, in step S40, the control circuit 50B controls the high-frequency generating circuit 52 to stop the high-frequency output.

FIGS. 19A to 19C are timing charts showing a state of changing the anatomy resistance and a state of the solution supply of the solution supply tube in accordance with the operation of the foot switch 7 and the pinch valve 8.

Referring to FIGS. 19A to 19C, when the on/off pedal of the foot switch 7 is off, the control circuit 50B does not detect the anatomy resistance and turns off the power supply to the pinch valve 8. Therefore, the solution supply tube 4 supplies the solution.

When the on/off pedal of the foot switch 7 is on, the energization starts and the bubbles are generated from the electrode 22. However, just after the on-operation of the on/off pedal of the foot switch 7, a small amount of bubbles is generated in the electrode 22 and the resistance Z as the anatomy resistance is lower than 500 Ω.

Thus, the control circuit 50B turns on power to the pinch valve 8 and stops the solution supply of the solution supply tube 4.

After the on/off pedal of the foot switch 7 is on and some time passes, the amount of bubbles to be adhered to the electrode 22 is large and the resistance Z increases. When the resistance Z is 500 Ω, the entire periphery of the electrode 22 is covered with the bubbles and the discharge operation has already been started. Then, as mentioned above, the control circuit 50B stops the power supply to the pinch valve 8 and restarts the solution supply of the solution supply tube 4.

When a coagulating pedal of the foot switch 7 is pressed and the coagulation set by a setting panel (not shown) of the high-frequency power supply 5B is caused by non-discharge operation, the control circuit 50B ignores steps S32 to S37. When the coagulating pedal of the foot switch 7 is pressed and the coagulation set by the setting panel (not shown) of the high-frequency power supply 5B is caused by the discharge operation, the control circuit 50B performs processing in steps S32 to S37, similarly to the case of pressing the on/off pedal.

Referring to FIG. 17, the power is supplied to the pinch valve 8 from the high-frequency power supply 5B, the solution supply tube pressing portion 82 presses the solution supply tube 4 to the solution supply tube supporting portion 81, and temporarily stops the solution supply.

When the solution supply temporarily stops and the deterioration in field of view of the resectoscope 2 is remarkable, the control circuit 50B may reduce the voltage of the power supplied to the pinch valve 8 so that the solution supply tube pressing portion 82 completely does not press out the solution supply tube 4, thereby reducing the solution supply, not stopping the solution supply.

With the structure and operation, the pinch valve 8 and the high-frequency power supply 5B become promotion holding portions which promote the generation of bubbles near the electrode 22 or hold the bubbles.

The pinch valve 8 and the high-frequency power supply 5B become solution stop portions which temporarily stop the solution supply of the solution supply device.

The control circuit 50B and the A/D converter 57 temporarily stop the solution supply of the solution supply device based on the information from measuring portion.

The solution supply tube 4 as a part of the solution supply device is a flexible solution supply tube and the solution supply stop portion presses a part of the solution supply tube.

According to the third embodiment, the high-frequency power supply 5B starts the output and then is covered with the bubbles of the electrode 22. The solution supply of the solution supply tube 4 stops until the discharge operation starts. Thus, the temperature of the solution near the electrode 22 increases and the bubbles are easily generated. Further, since the bubbles near the electrode 22 are not scattered by the solution supply, the entire electrode 22 is covered with the bubbles and the discharge operation starts by low power and the body anatomy is resected, is transpired, and is discharged and coagulated. Thus, in the case of using the physiological saline which is supplied in the coelom of the body for a long time as the conductive solution, the high-frequency power supply with low power is used, the manufacturing costs of the electric operation apparatus are reduced, and the power consumption is saved.

Figure 20:
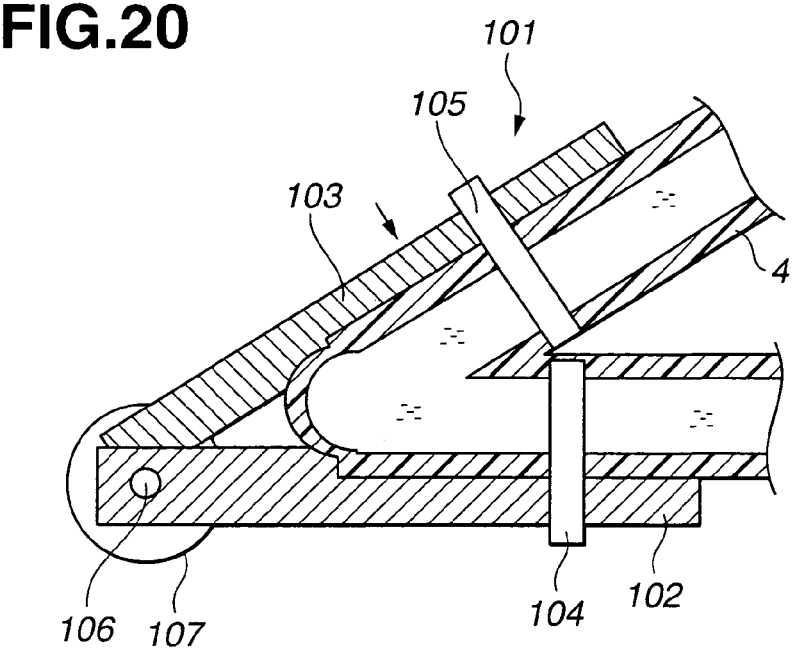
FIG. 20 is a side view showing a lever according to a first modification of the third embodiment.

FIG. 20 is a side view showing a lever according to a first modification of the third embodiment.

Referring to FIG. 20, a lever 101 comprises a solution supply tube supporting portion 102 in place of the pinch valve 8 shown in FIG. 14, and a movable solution supply tube pressing portion 103 which is fixed by a single rotating shaft 106.

The solution supply tube 4 is externally fixed to the solution supply tube supporting portion 102 by a tube fixing portion 104. The solution supply tube 4 is externally fixed to the solution supply tube pressing portion 103 by a tube fixing portion 105.

In the lever 101, the power from the high-frequency power supply 5B rotates a motor 107, the rotating shaft 106 and the solution supply tube pressing portion 103 are rotated in accordance with the rotation of the motor 107, and the solution supply tube 4 is bent, thereby stopping the solution supply. The operation timing of the lever 101 is the same as the timing in the case of using the pinch valve 8.

Similarly to the case using the pinch valve 8, when the field of view of the resectoscope 2 deteriorates, the solution supply tube 4 is not completely bent and only the amount of supplied solution may be reduced.

With the above structure, the solution supply tube supporting portion 102 is a fixing portion which fixes the solution supply tube 4 of the solution supply tube.

The solution supply tube pressing portion 103 is a movable lever portion which bends the solution supply tube that is attached to the fixing portion by the single supporting point.

The motor 107 is a lever operating portion which operates a lever portion.

According to the first modification, the same advantages as those according to the third embodiment are obtained.

Figure 21:
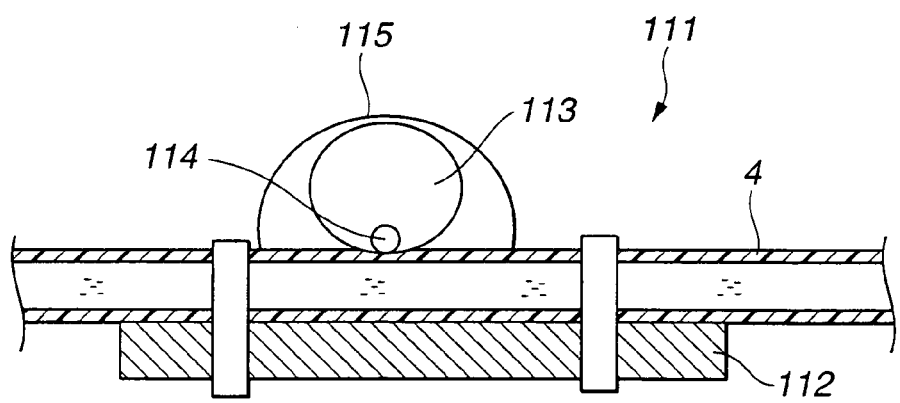
FIG. 21 is a side view when the solution supply of a rotary solenoid is not stopped according to a second modification of the third embodiment.
Figure 22:
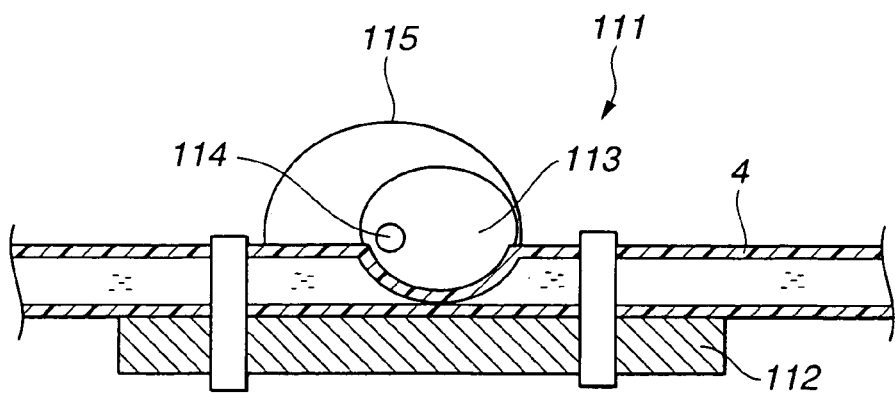
FIG. 22 is a side view when the solution supply of the rotary solenoid is stopped, differently from the case shown in FIG. 21.

FIGS. 21 and 22 show a second modification of the third embodiment. FIG. 21 is a side view when the solution supply of a rotary solenoid does not stop. FIG. 22 is a side view when the solution supply of the rotary solenoid stops.

Referring to FIGS. 21 and 22, a rotary solenoid 111 comprises: a solution supply tube supporting portion 112 in place of the pinch valve 8; a solution supply tube pressing portion 113; a rotating shaft 114 which is eccentric to the solution supply tube pressing portion 113 and is attached; and a solenoid valve 115 which rotates the rotating shaft 114.

In the case of using the rotary solenoid 111, the power from the high-frequency power supply 5B rotates the solenoid valve 115 and, in accordance therewith, the rotating shaft 114 and the solution supply tube pressing portion 113 rotate. Referring to FIG. 22, the rotary solenoid 111 presses the solution supply tube 4, thereby stopping the solution supply. The operation timing is the same as that using the pinch valve 8. Similarly to the case of using the pinch valve 8, when the field of view of the resectoscope 2 deteriorates, the rotary solenoid 111 does not completely press the solution supply tube 4 and only the amount of supplied solution may be reduced.

With the above structure, the solution supply tube supporting portion 112 is a fixing portion which fixes the solution supply tube 4 of the solution supply tube.

The solution supply tube pressing portion 113 is a pressing portion which presses the solution supply tube.

The solenoid valve 115 is a rotating portion which rotates the pressing portion connected by the pressing portion and the rotating shaft 114.

(Fourth Embodiment)

Figure 23:
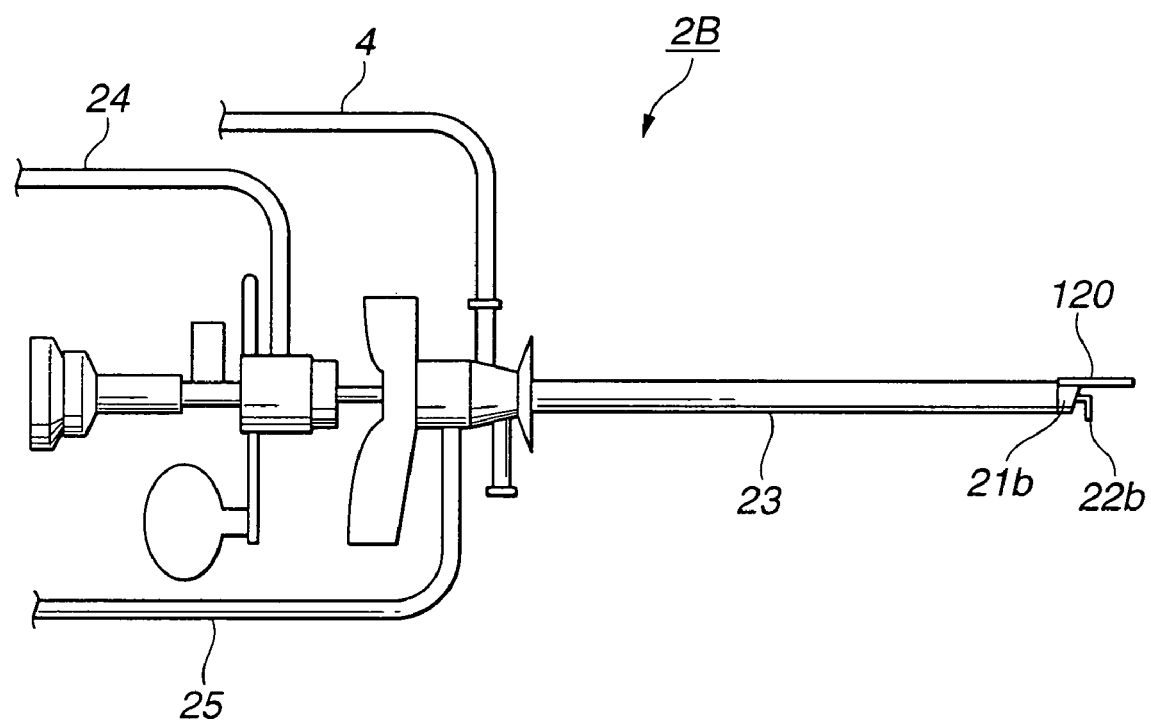
FIG. 23 is a side view showing a resectoscope according to a fourth embodiment.
Figure 24:
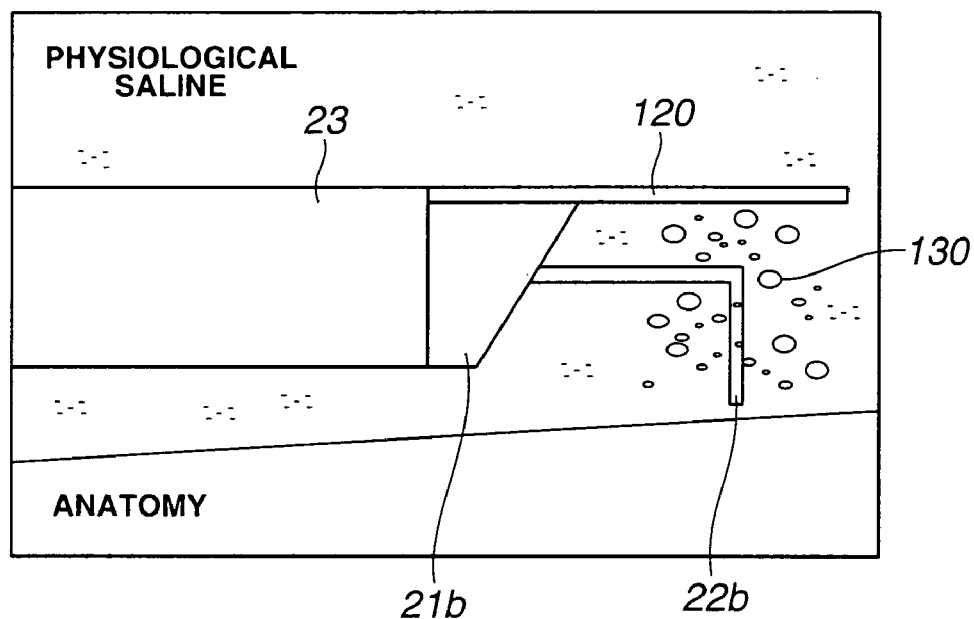
FIG. 24 is one enlarged view showing an edge of the resectoscope shown in FIG. 23.
Figure 25:
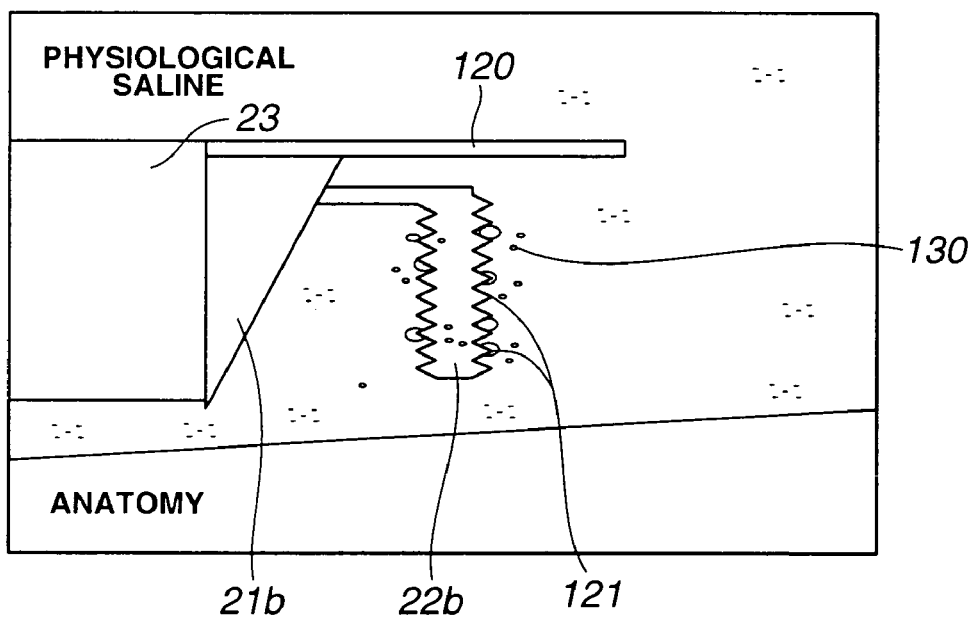
FIG. 25 is another further-enlarged view showing the edge of the resectoscope shown in FIG. 24.

FIGS. 23 to 25 are diagrams according to a fourth embodiment.

The structure according to the fourth embodiment is almost the same as that according to the third embodiment. Thus, only different portions are described, the same components are designated by the same reference numerals, and a description thereof is omitted.

Referring to FIGS. 23 to 25, according to the fourth embodiment, an edge portion 21*b* of a resectoscope 2B has a cover 120 which covers the top of an electrode 22*b*.

Referring to FIG. 25, a minute projection 121 is arranged on the surface of the electrode 22*b*.

With the above structure, the cover 120 covers at least one direction of the electrode 22*b*. The cover 120 is a solution holding portion which holds, near the electrode 22*b*, solution heated near the electrode 22*b*. Further, the cover 120 is a portion which generates bubbles 130 near the electrode 22*b* or holds the bubbles 130.

The projection 121 is a projecting portion which is arranged to the electrode 22*b*. The projection 121 is a bubble adhering portion where the bubbles 130 generated near the electrode 22*b* are adhered to the electrode 22*b*. The projection 121 is a portion which holds the generation of the bubbles 130 near the electrode 22*b* or holds the bubbles 130.

The operations with the structure will be described according to the fourth embodiment.

The operation of the control circuit 50B is indicated as a flowchart shown in FIG. 20.

In step S33, the control circuit 50B outputs the high frequency and, then, the solution supply stops similarly to the case according to the third embodiment. Then, the heated physiological saline is collected near the electrode 22*b* by the cover 120. Further, the generated bubbles 130 are sealed by the cover 120 so as not to ascend.

The bubbles 130 adhere to the minute projection 121 on the surface of the electrode 22*b* and cover the electrode 22*b*. As a result, the sufficient amount of the bubbles 130 is collected near the electrode 22 by the low output power and the discharge operation starts.

As mentioned above, according to the fourth embodiment, the cover 120 for covering the electrode 22*b* is arranged and, therefore, the temperature of physiological saline near the electrode 22*b* is easily increased. The generated bubbles 130 do not ascend. Further, since the surface of the electrode 22*b* has the projection 121 for adhering the bubbles 130, the lower power generates the bubbles 130 for covering the entire electrode 22*b* and, consequently, the discharge operation starts by the lower power, thus, the body anatomy is resected, is transpired, and is discharged and coagulated.

(Fifth Embodiment)

FIGS. 26 to 31C are diagrams according to a fifth embodiment.

The structure according to the fifth embodiment is almost the same as that according to the first embodiment and only different points are described.

Figure 26:
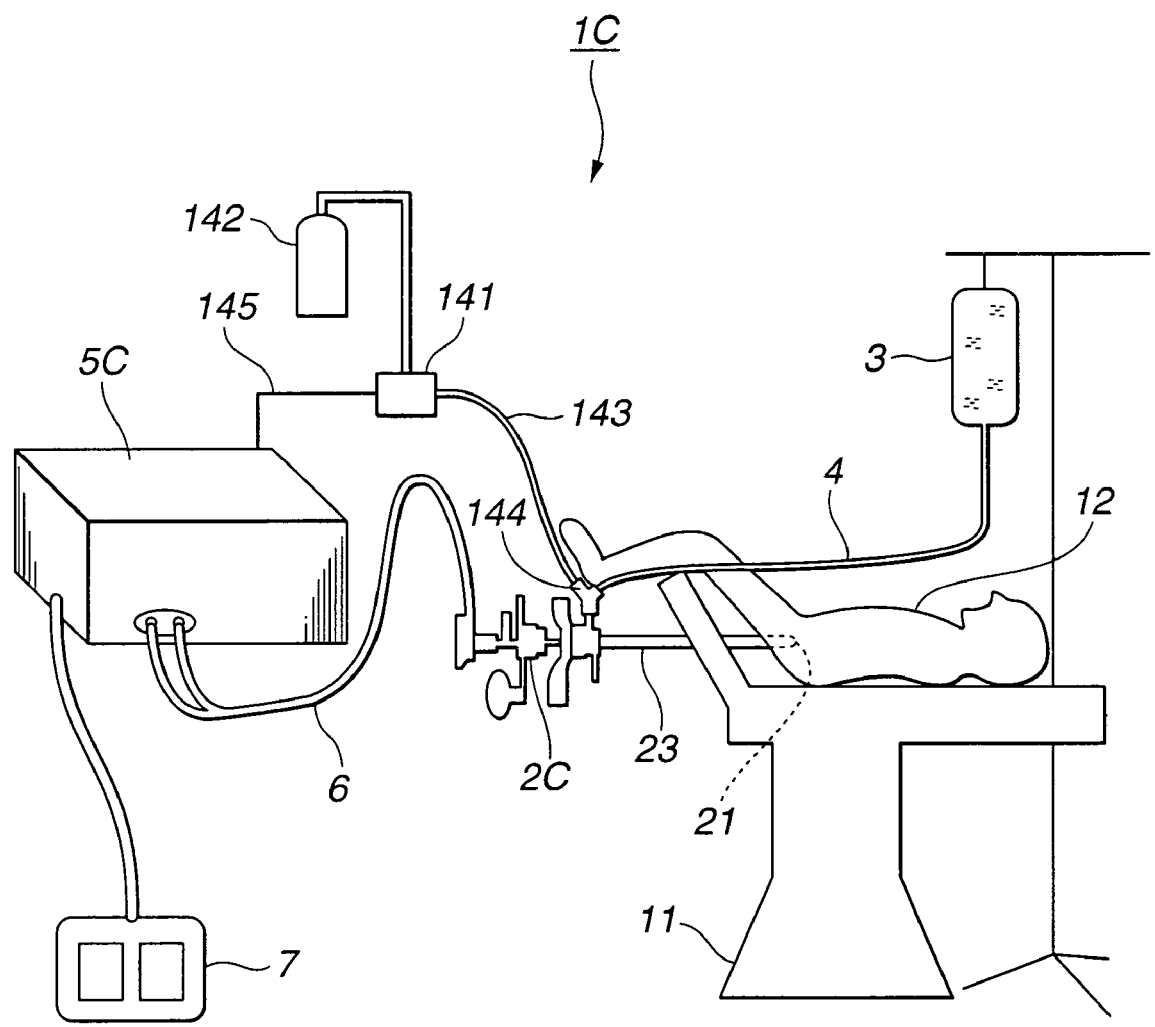
FIG. 26 is a diagram showing the entire structure of an electric operation apparatus according to a fifth embodiment.

Referring to FIG. 26, according to the fifth embodiment, an electric operation apparatus 1C comprises: a resectoscope 2C; a high-frequency power supply 5C; a valve 141; a gas cylinder 142; an air supply tube 143; and a Y-shaped tube 144.

The valve 141 and the gas cylinder 142 are connected to the resectoscope 2C via the air supply tube 143 which is branched by the Y-shaped tube 144 from the solution supply tube 4. The valve 141 is attached to the air supply tube 143. The valve 141 includes a valve for reducing the pressure. The gas cylinder 142 supplies gas to the air supply tube 143.

The high-frequency power supply 5C supplies power to the valve 141 via a valve cable 145.

The high-frequency power supply 5C controls the valve 141 only when the discharge operation does not start in the electrode after outputting the high-frequency current, and it supplies air via the air supply tube 143.

The high-frequency power supply 5C automatically controls the valve 141 to stop the air supply via the air supply tube 143 when the discharge operation starts in the electrode.

Figure 27:
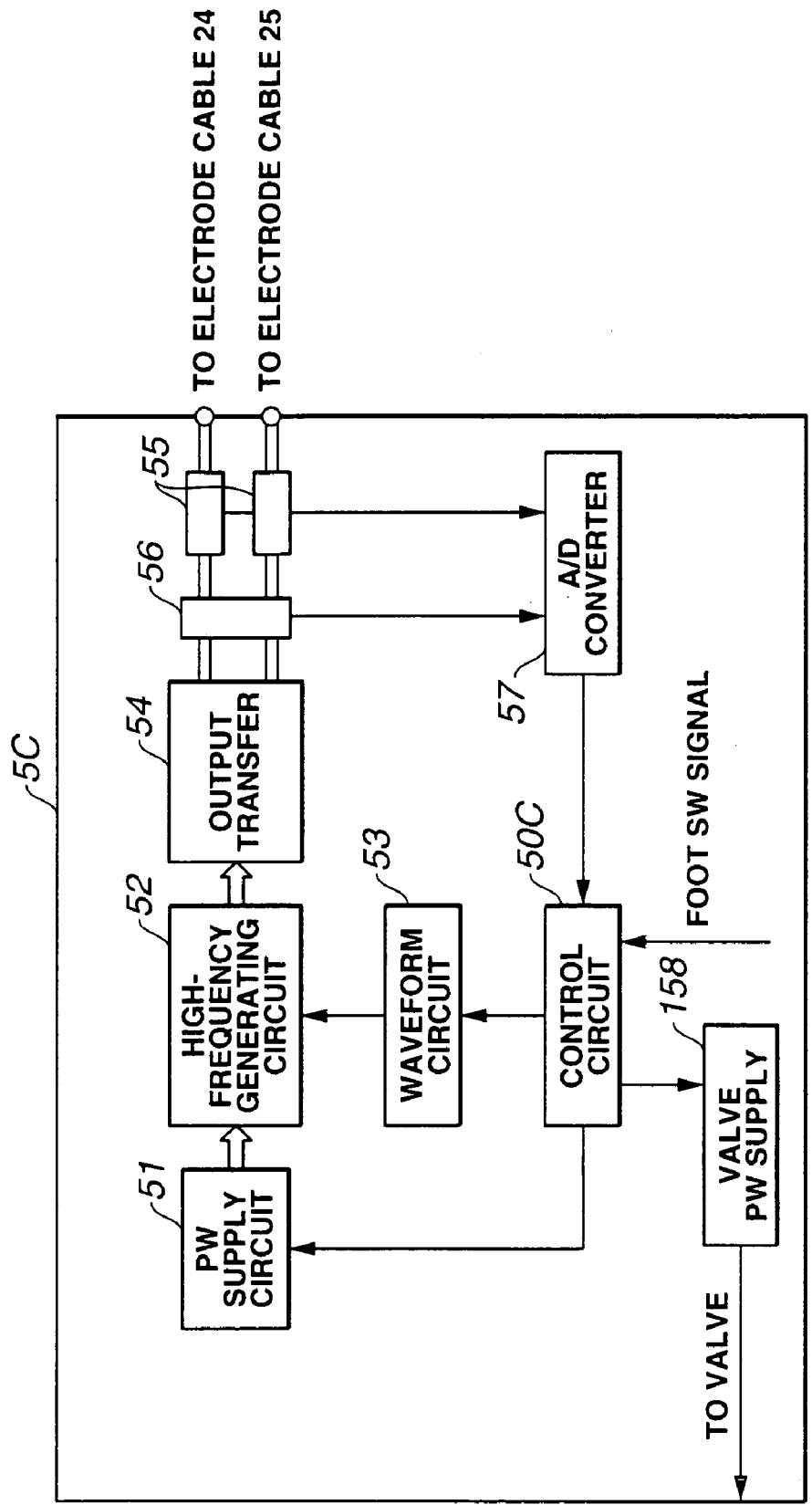
FIG. 27 is a circuitry block diagram showing a high-frequency power supply shown in FIG. 26.

Referring to FIG. 27, the high-frequency power supply 5C has a valve power supply 158. The control circuit 50C controls the power supply circuit 51 and the waveform circuit 53 based on the digital data from the A/D converter 57 and the signal from the foot switch 7. Further, the control circuit 50C controls the valve power supply 158 which supplies power to the valve 141.

Figure 28:
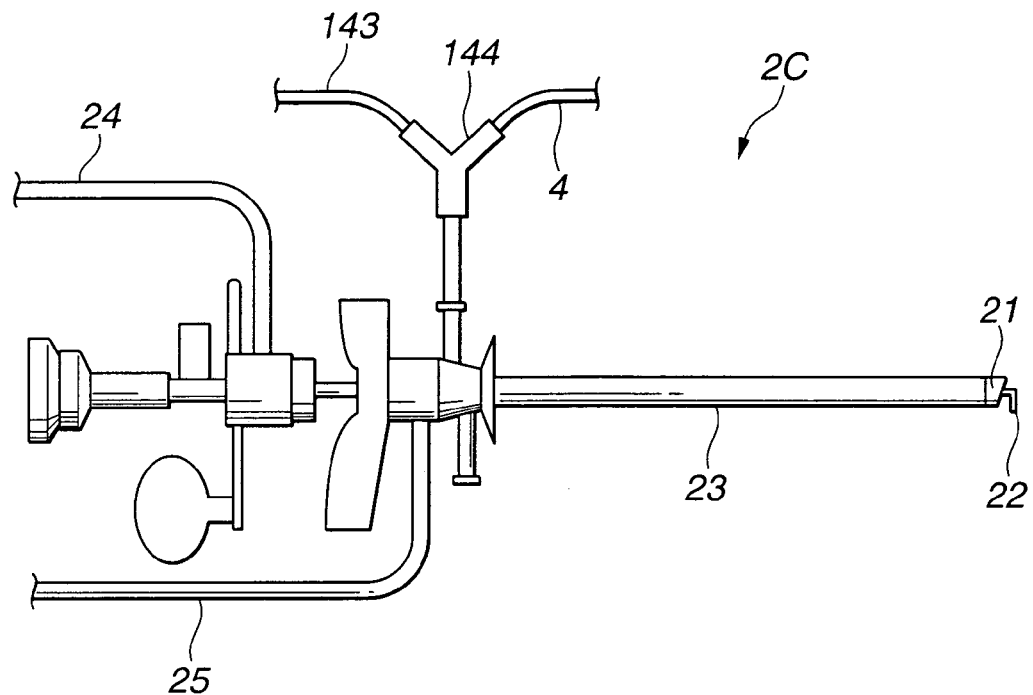
FIG. 28 is an external view showing the resectoscope shown in FIG. 26.

Referring to FIG. 28, the resectoscope 2C comprises the electrode cable 24 which is conductive to the electrode 22 of the edge portion 21 thereof and the electrode cable 25 which is conductive to the coating tube 23. Further, the air supply tube 143 branched from the solution supply tube 4 by the Y-shaped tube 144 is connected to the resectoscope 2C.

Figure 29:
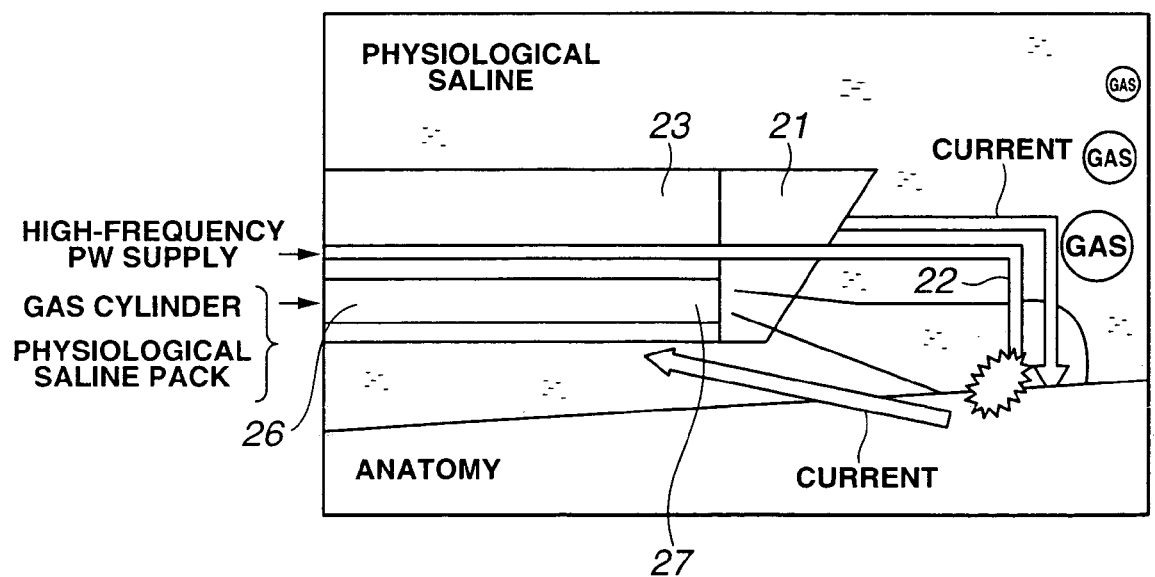
FIG. 29 is an enlarged view showing an edge of the resectoscope shown in FIG. 28.

Referring to FIG. 29, the physiological saline from the physiological saline pack 3 is transmitted from the air and solution supply vent 27 and gas from the gas cylinder 142 is supplied at the edge portion 21 of the resectoscope 2C.

In a state shown in FIG. 29, the electrode 22 is covered with gas by supplying air from the air and solution supply vent 27. Thus, the gas from the air and solution supply vent 27 promotes the discharge operation of the electrode 22 upon generating the high-frequency current.

The operation with the above structure will be described according to the fifth embodiment.

FIG. 30 is a flowchart showing the operation of the control circuit 50C.

Referring to FIG. 30, in step S51, the on/off pedal of the foot switch 7 is pressed. In step S52, the control circuit 50C controls the high-frequency generating circuit 52 to output the high frequency.

Next, in step S53, the control circuit 50C fetches the current value of the current sensor 55 via the A/D converter 57. In step S54, the control circuit 50C fetches the voltage value of the voltage sensor 56 via the A/D converter 57.

After that, in step S55, the control circuit 50C divides the voltage value fetched therein by the current value, thereby calculating the resistance Z between the electrode 22 and the coating tube 23. Then, the processing routine shifts to step S56.

In step S56, when the resistance value Z is higher than 500 Ω, the control circuit 50C determines that the entire electrode 22 is covered with the bubbles and the discharge operation has already been started. Then, the control circuit 50C does not supply the gas via the air and solution vent 27 and the processing routine shifts to step S61.

In step S56, the control circuit 50C determines that the resistance Z is lower than 500 Ω. In step S57, the control circuit 50C measures whether or not time of 0.5 sec passes. When the measurement result is shorter than 0.5 sec, the processing routine returns to step S53 and the similar processing is repeated.

When the measurement result is 0.5 sec or longer, in step S57, the control circuit 50C determines that the discharge operation does not start. Then, in step S58, the control circuit 50C controls the valve power supply 158 to turn on the valve 141. Thus, the gas supply starts and the discharge operation is promoted. In this case, any type of gas can be used if it is gas which promotes the discharge operation, such as argon gas. In addition to the direct gas supply, the gas may be generated by using blowing agent.

Thereafter, in step S59, the control circuit 50C determines that the resistance Z is lower than 500 Ω. Then, the control circuit 50 returns to step S58. When the control circuit 50C determines that the resistance Z is not less than 500 Ω and the discharge operation starts, in step S60, the control circuit 50C controls the valve power supply 158 to turn off the valve 141 and stops the air supply. Then, the processing routine shifts to step S61.

In step S61, the on/off pedal of the foot switch 7 is not pressed. In step S62, the control circuit 50C controls the high-frequency generating circuit 52 to stop the output of high frequency.

Figures 31A, 31B, 31C:
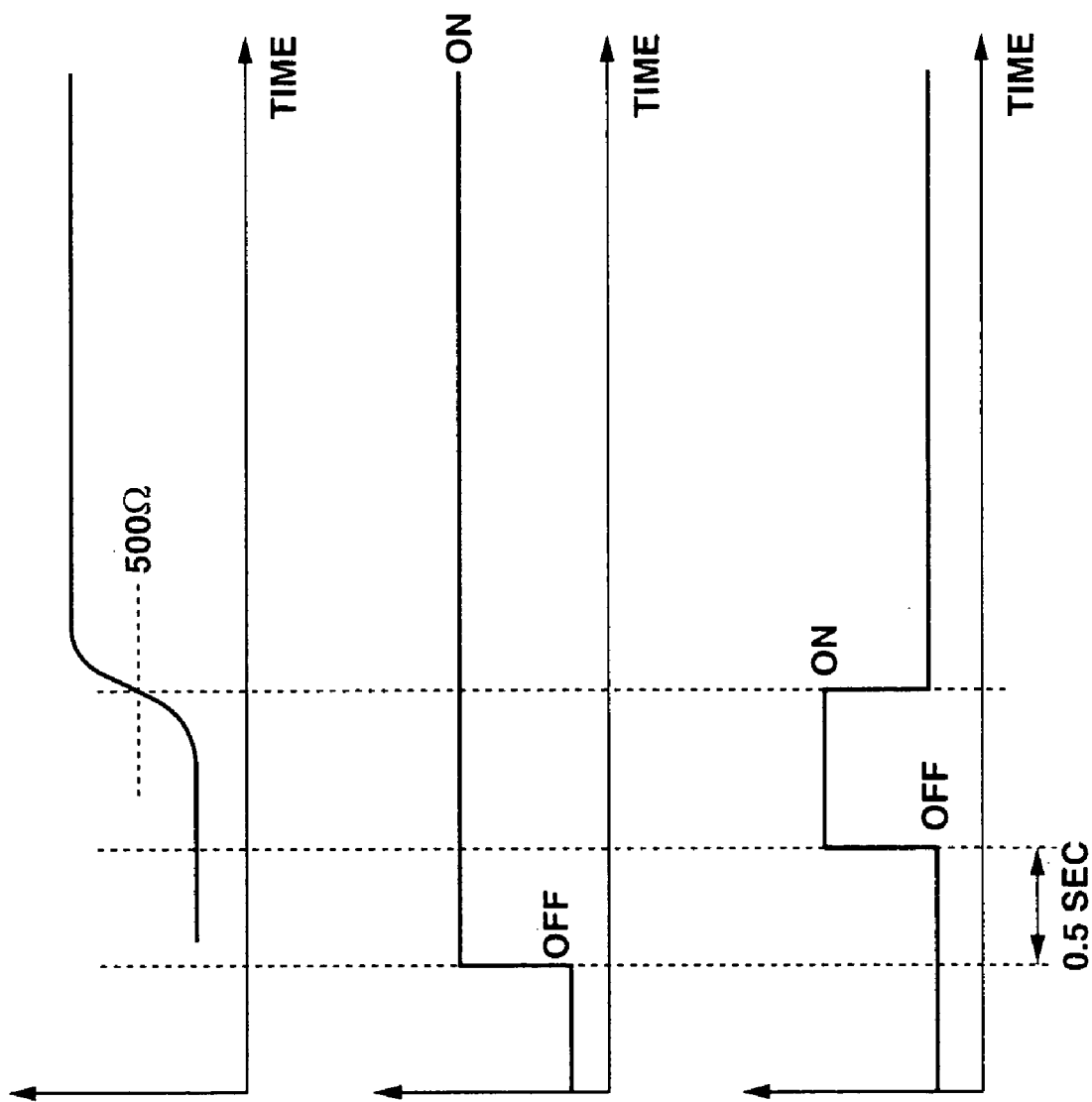
FIG. 31A is a timing chart showing how the resistance in the anatomy changes in the passage of time based on the flowchart shown in FIG. 30.
FIG. 31B is a timing chart showing the operation of a foot switch based on the flowchart shown in FIG. 30.
FIG. 31C is a timing chart showing the operation timing of a valve based on the flowchart shown in FIG. 30.

FIGS. 31A to 31C are timing charts showing a state for the change in anatomy resistance, the operation of the foot switch 7, and the operation timing of the valve 141 with reference to the flowchart shown in FIG. 30.

Referring to FIGS. 31A to 31C, when the on/off pedal of the foot switch 7 is off, the anatomy resistance is not detected, the power supply to the valve 141 is off, and the gas is not supplied via the air supply tube 143.

The on/off pedal of the foot switch 7 is on and, then, the bubbles are generated from the electrode 22. However, just after the on/off pedal of the foot switch 7 is on, a small amount of bubbles is generated in the electrode 22 and the resistance Z of the anatomy resistance is lower than 500 Ω.

After the on/off pedal is on and 0.5 sec passes, the control circuit 50C turns on the power supply to the valve 141 and the gas is transmitted via the air supply tube 143.

The on/off pedal of the foot switch 7 is on, the gas is transmitted via the air supply tube 143, and some time passes, the gas supply promotes the discharge operation in the electrode 22 and the resistance Z increases.

When the resistance Z is 500 Ω, the discharge operation has already started. The control circuit 50C turns off the power supply to the valve 141 and stops the gas transmission via the air supply tube 143.

With the structure and the operation, the valve 141, the gas cylinder 142, and the air supply tube 143 are air supply devices for supplying the gas near the electrode 22, and also function as discharge promoting portions which promote the discharge operation in the electrode 22.

The gas supply of the gas cylinder 142 is a portion for promoting the discharge operation in the electrode 22 upon generating the high-frequency current.

The control circuit 50C is a control portion for on/off operation of the air supply to the air supply devices.

According to the fifth embodiment, the gas supply promotes the discharge operation in the electrode 22. Only in the case that the discharge operation does not start in the electrode 22 even though some time passes from the time when the high-frequency power supply 5C starts to output, the gas is supplied. After the start of discharge operation, the gas supply stops.

Consequently, according to the fifth embodiment, the amount of supplied air and the air supply time are suppressed to the necessary and minimum level and the low power enables the anatomy to be resected, be transpired, and be discharged and coagulated in the conductive solution. Therefore, according to the fifth embodiment, the high power is not necessary and, even when using the physiological saline which is supplied in the coelom of the body as the conductive solution for a long time, the high-frequency power supply may be used with the low power. Therefore, according to the fifth embodiment, the manufacturing costs of the electric operation apparatus are reduced and the power consumption is saved. Further, according to the fifth embodiment, the amount of supplied air and the air supply time are supplied to the necessary and minimum level and therefore the field of view is not deteriorated due to the air supply.

Figure 32:
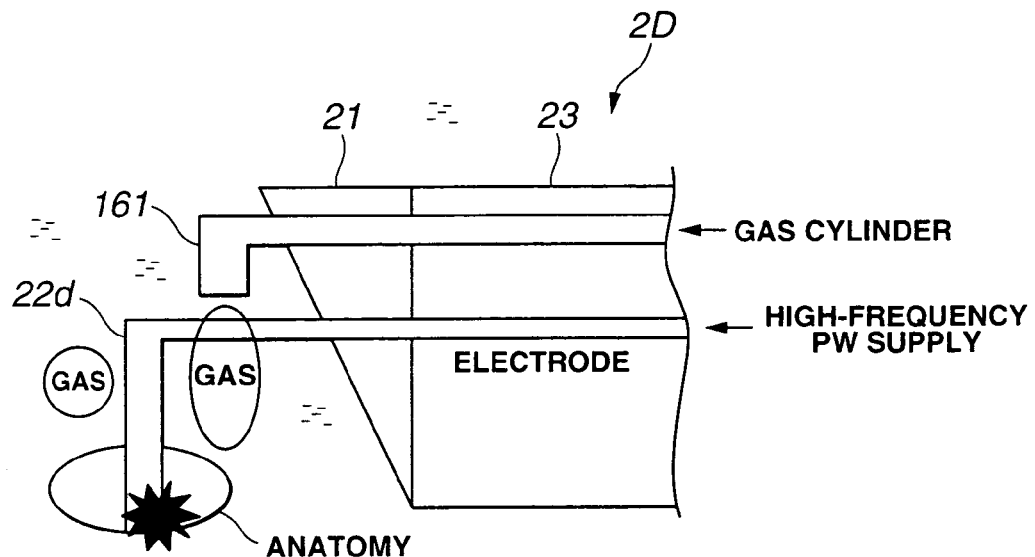
FIG. 32 is an enlarged view showing an edge of a resectoscope having an air supply nozzle according to a modification of the fifth embodiment.

FIG. 32 is an enlarged view of an edge of a resectoscope having an air supply nozzle according to a modification of the fifth embodiment. Portions not shown in FIG. 32 are described with FIGS. 26 to 28 in place.

Referring to FIG. 32, an electrode 22d and an air supply nozzle 161 are exposed from the edge portion 21 of a resectoscope 2D. In place of the air and solution supply vent 27 shown in FIG. 29, the resectoscope 2D has a solution supply vent (not shown) and the air supply nozzle 161 which can be slid forward and backward. The solution supply vent (not shown) transmits the physiological saline from the physiological saline pack 3.

The air supply nozzle 161 transmits gas from the gas cylinder 142. Further, the air supply nozzle 161 is arranged near the electrode 22d, having the edge side which is L-shaped in the side direction. The air supply nozzle 161 is slid forward and backward, thereby forward and backward adjusting the position to which gas is sprayed. In this case, the air supply nozzle 161 is slid forward and backward by the operation of an operating portion such as a lever provided for the base end side of the resectoscope 2D.

Other structures are the same as those according to the fifth embodiment.

According to the modification, the position to which the gas for promoting the discharge operation is sprayed is adjusted forward and backward corresponding to the shape of the anatomy to be treated. The low power enables the anatomy to be resected, be transpired, and be discharged and coagulated in the conductive solution.

(Sixth Embodiment)

Figure 33:
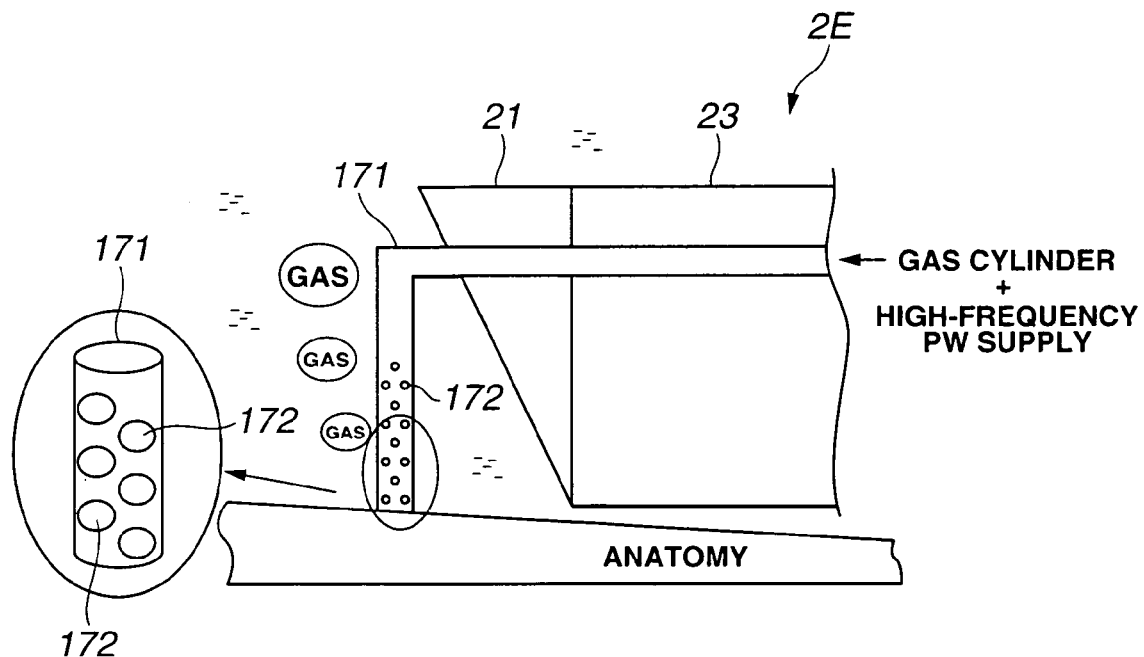
FIG. 33 is an enlarged view showing an edge of a resectoscope having an air supply nozzle according to a sixth embodiment.

FIG. 33 is a diagram according to a sixth embodiment.

According to the sixth embodiment, the structure is almost the same as that according to the fifth embodiment. Therefore, only different points are described. Further, the same reference numerals according to the fifth embodiment denote the same components and a description is not given. Portions shown in FIG. 33 are described with reference to FIGS. 26 to 28 in place.

Referring to FIG. 33, according to the sixth embodiment, a hollow electrode 171 is exposed from the edge portion 121 of a resectoscope 2E. In place of the air and solution supply vent 27 shown in FIG. 29, the resectoscope 2E comprises a solution supply vent (not shown) and a plurality of air supply holes 172 of the hollow electrode 171.

The hollow electrode 171 is bent to be L-shaped so that it easily comes into contact with the anatomy. Further, the hollow electrode 171 has a plurality of air supply holes 172 at its edge portion. The end near the hollow electrode 171 is connected to the gas cylinder 142 and the high-frequency power supply 5C shown in FIG. 26. The hollow electrode 171 transmits the gas from the gas cylinder 142 from the plurality of air supply holes 172 and receives the high-frequency output of the high-frequency power supply 5C.

The operation with the above structure will be described according to the sixth embodiment.

The operation of the control circuit 50C according to the sixth embodiment is almost the same as that according to the fifth embodiment. However, the valve 141 is released, the gas from the gas cylinder 142 is supplied, and the gas is then generated from the plurality of air supply holes 172 at the edge portion of the hollow electrodes 171. A small amount of gas covers the periphery of the hollow electrode 171. Therefore, the discharge operation starts immediately and the operation is possible.

According to the sixth embodiment, since the air for promoting the discharge operation in the electrode is supplied from the electrode, the time until the start of discharge operation is short and the low power enables the discharge operation. Further, the gas is generated only by the edge portion of the electrode and therefore the deterioration in field of view due to the gas is prevented.

According to the sixth embodiment, the edge portion of the hollow electrode 171 has a plurality of air supply holes 172. However, the present invention is not limited to this and the single air supply holes 172 may be formed at the edge portion of the hollow electrode 171.

(Seventh Embodiment)

FIGS. 34 to 42C are diagrams according to the seventh embodiment.

Figure 34:
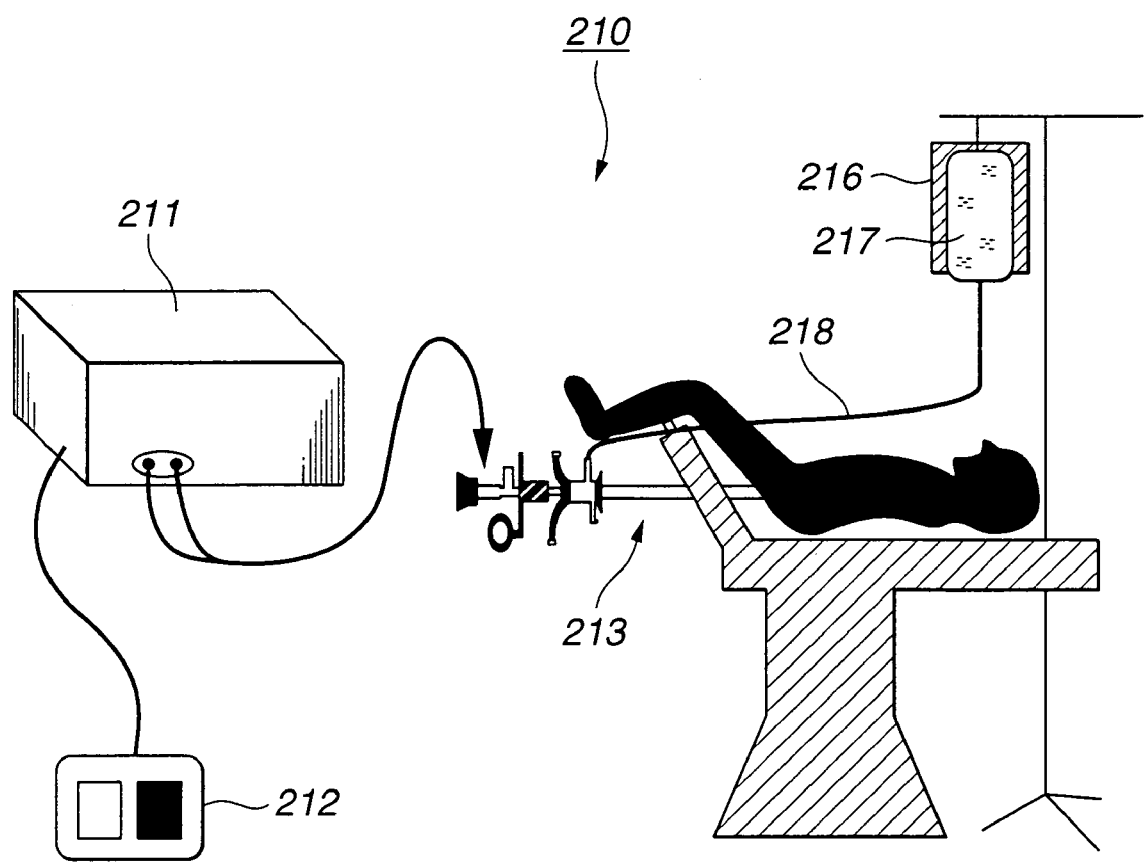
FIG. 34 is a diagram showing the entire structure of an electric operation apparatus according to a seventh embodiment.

Referring to FIG. 34, an electric operation apparatus 210 according to the seventh embodiment comprises a high-frequency power supply 211 as a high-frequency generating device which outputs high-frequency current for treating the diseased part, and a resectoscope 213 which supplies the high-frequency current from the high-frequency power supply 211 and treats the diseased part.

A foot switch 212 for controlling the on/off operation of the high-frequency output is connected to the high-frequency power supply 211. A physiological saline pack 217 heated by a heater 216 is connected to the resectoscope 213 via a solution supply tube 218.

Figure 36:
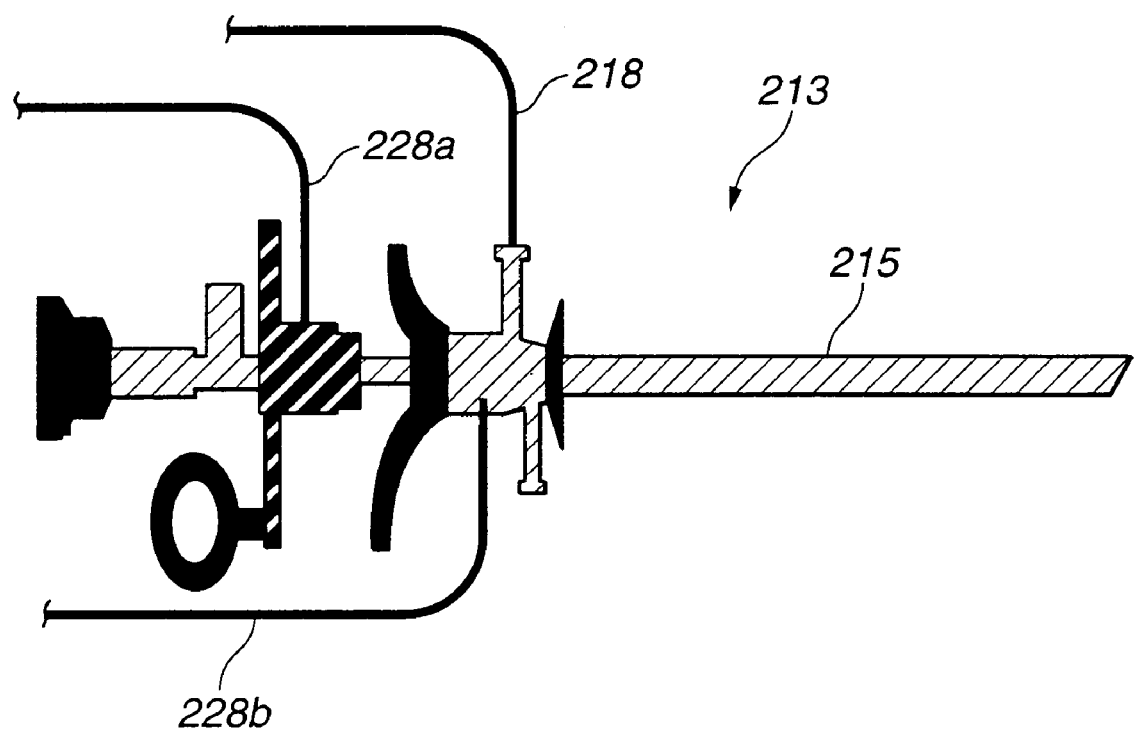
FIG. 36 is an external view showing the resectoscope shown in FIG. 34.

The high-frequency power supply 211 is connected to an active electrode 214 attached to its edge via the resectoscope 213 and to a coating tube 215 as a return electrode of the resectoscope 213 (refer to FIG. 36).

Figure 35:
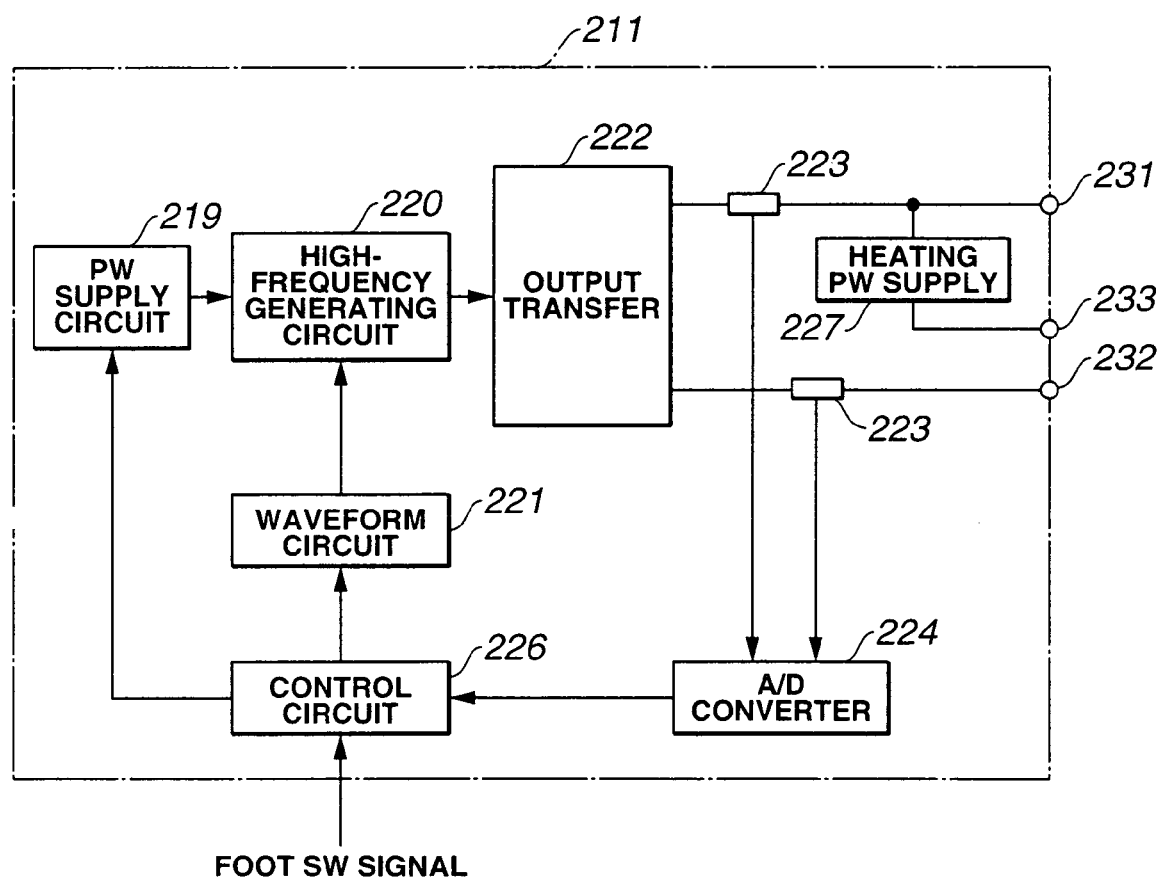
FIG. 35 is a circuitry block diagram showing a high-frequency power supply shown in FIG. 34.

Referring to FIG. 35, the high-frequency power supply 211 comprises: a power source circuit 211 for supplying DC current; a high-frequency generating circuit 220 for converting the DC current from the power supply circuit 211 to the high-frequency current; a waveform circuit 221 for instructing a waveform of the high-frequency current to the high-frequency generating circuit 220; an output transfer 222 which outputs the high-frequency current from the high-frequency generating circuit 220 to the resectoscope 213; a current sensor 223 for detecting the output current from the output transfer 222; an A/D converter 224 for converting a signal from the current sensor 223 into a digital signal; a control circuit 226 as a control device for controlling the power supply circuit 211 and the waveform circuit 221 based on the digital data from the A/D converter 224 and on the signal from the foot switch 212; and a heating power supply 227 as a heating power supply device for heating the active electrode 214.

A first active terminal 231 as one terminal of the output transfer 222 is connected to one end of the active electrode 214. On the other hand, a return terminal 232 as another terminal of the output transfer 222 is connected to the coating tube 215 of the resectoscope 213.

Further, one terminal of the heating power supply 227 is connected to the first active terminal 231 connected to the one end of the active electrode 214. On the other hand, the other terminal of the heating power supply 227 is connected to the second active terminal 233 connected to the other end of the active electrode 214.

Referring to FIG. 36, connected to the resectoscope 213 are an electrode cable 228a conductive to the active electrode 214 at its edge, and an electrode cable 228b conductive to the coating tube 215 of the resectoscope 213.

Figure 37:
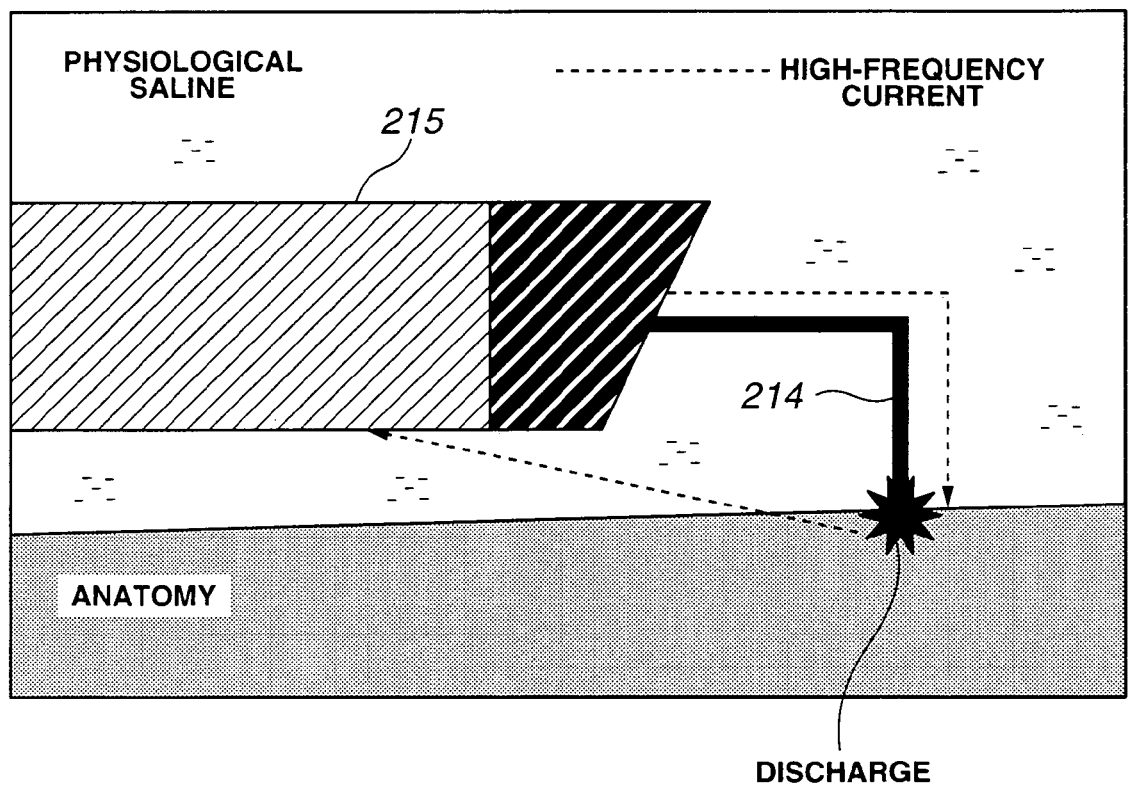
FIG. 37 is an enlarged view showing an edge of the resectoscope shown in FIG. 36.

FIG. 37 shows an edge portion of the resectoscope 213.

The active electrode 214 is exposed from the edge of the resectoscope 213. The high-frequency current outputted from the active electrode 214 is collected to the coating tube 215 via the physiological saline.

Figure 38:
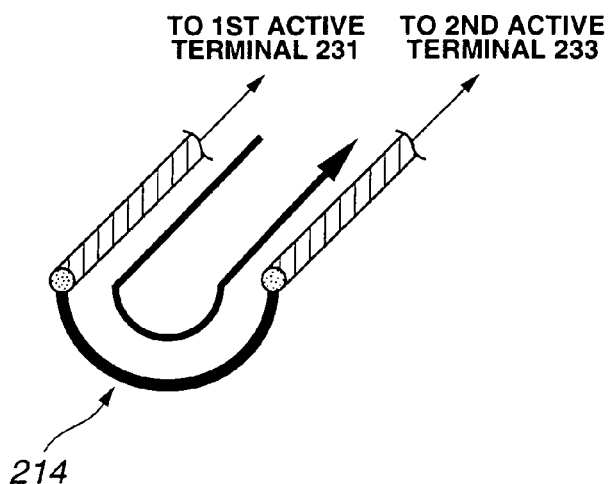
FIG. 38 is a diagram showing a first edge structure of an active electrode shown in FIG. 37.

FIG. 38 is a diagram showing the structure of an edge of the active electrode 214.

The active electrode 214 is made of a material having resistance about 30 Ω.

The heating current is outputted from the heating power supply 227 and then the active electrode 214 is heated because the power consumed in a loop portion increases upon flowing the current from the first active terminal 231 to the second active terminal 233.

Figure 39:
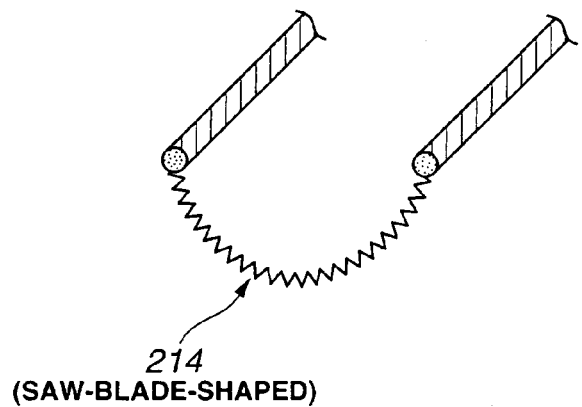
FIG. 39 is a diagram showing a second edge structure of the active electrode shown in FIG. 37.
Figure 40:
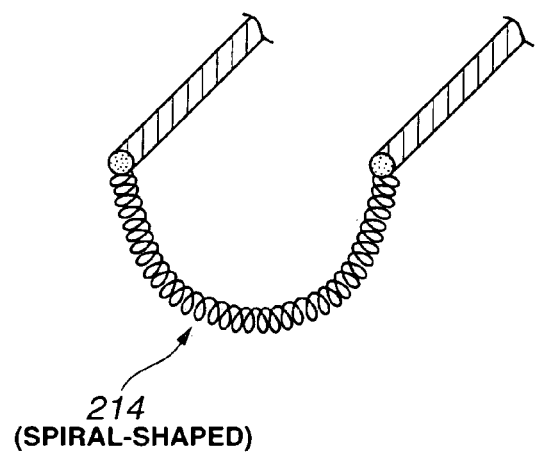
FIG. 40 is a diagram showing a third edge structure of the active electrode shown in FIG. 37.

FIGS. 39 and 40 are diagrams showing the structure of the edge of the active electrode 214, similarly to FIG. 38. The active electrode 214 shown in FIGS. 39 and 40 is saw-blade-shaped or is spiral-structured and, consequently, the consumption power is increased at the edge of the active electrode 214 and it is heated.

The operation with the above structure will be described according to the seventh embodiment.

Figure 41:
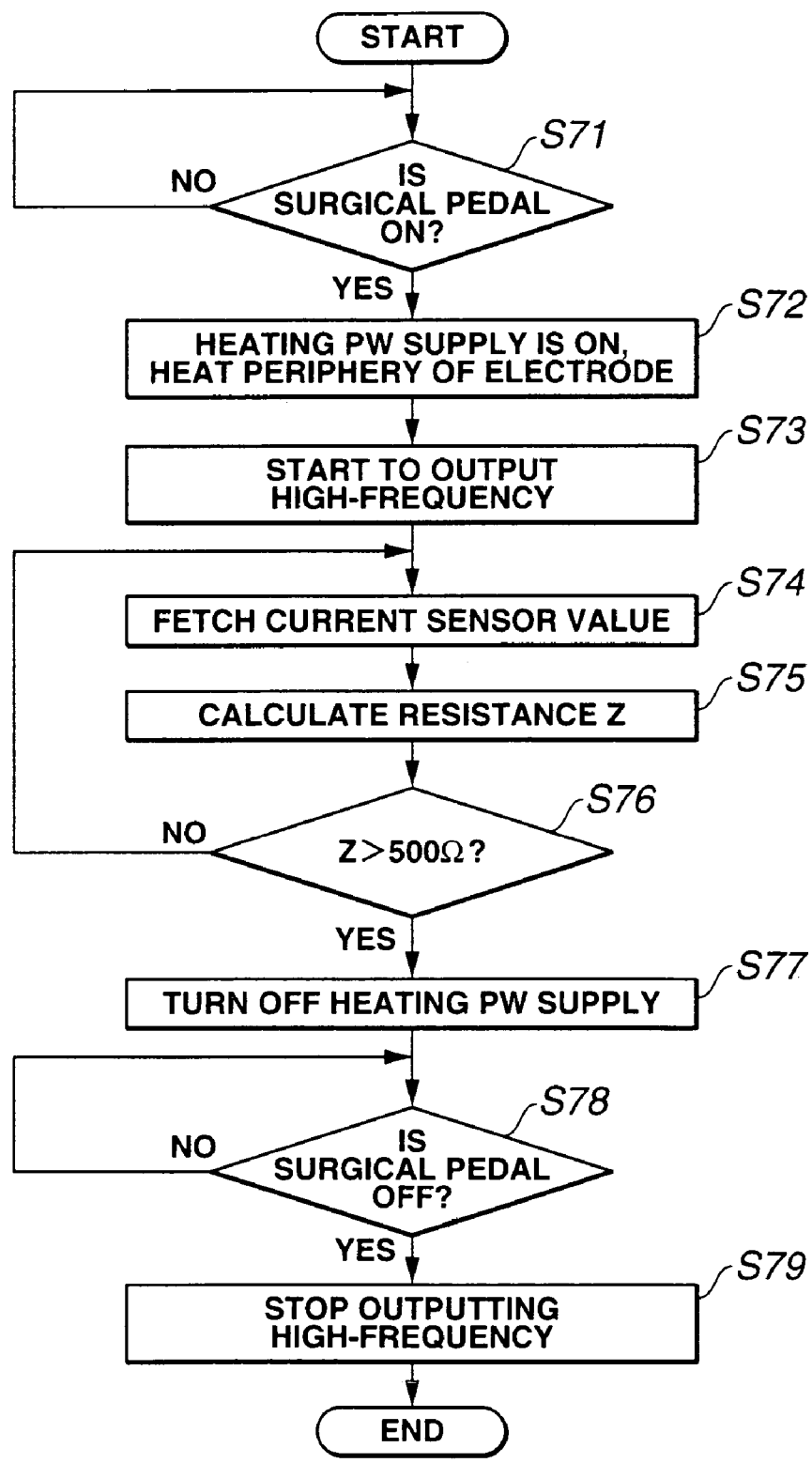
FIG. 41 is a flowchart showing the control operation of a control circuit according to a seventh embodiment.
Figure 42:
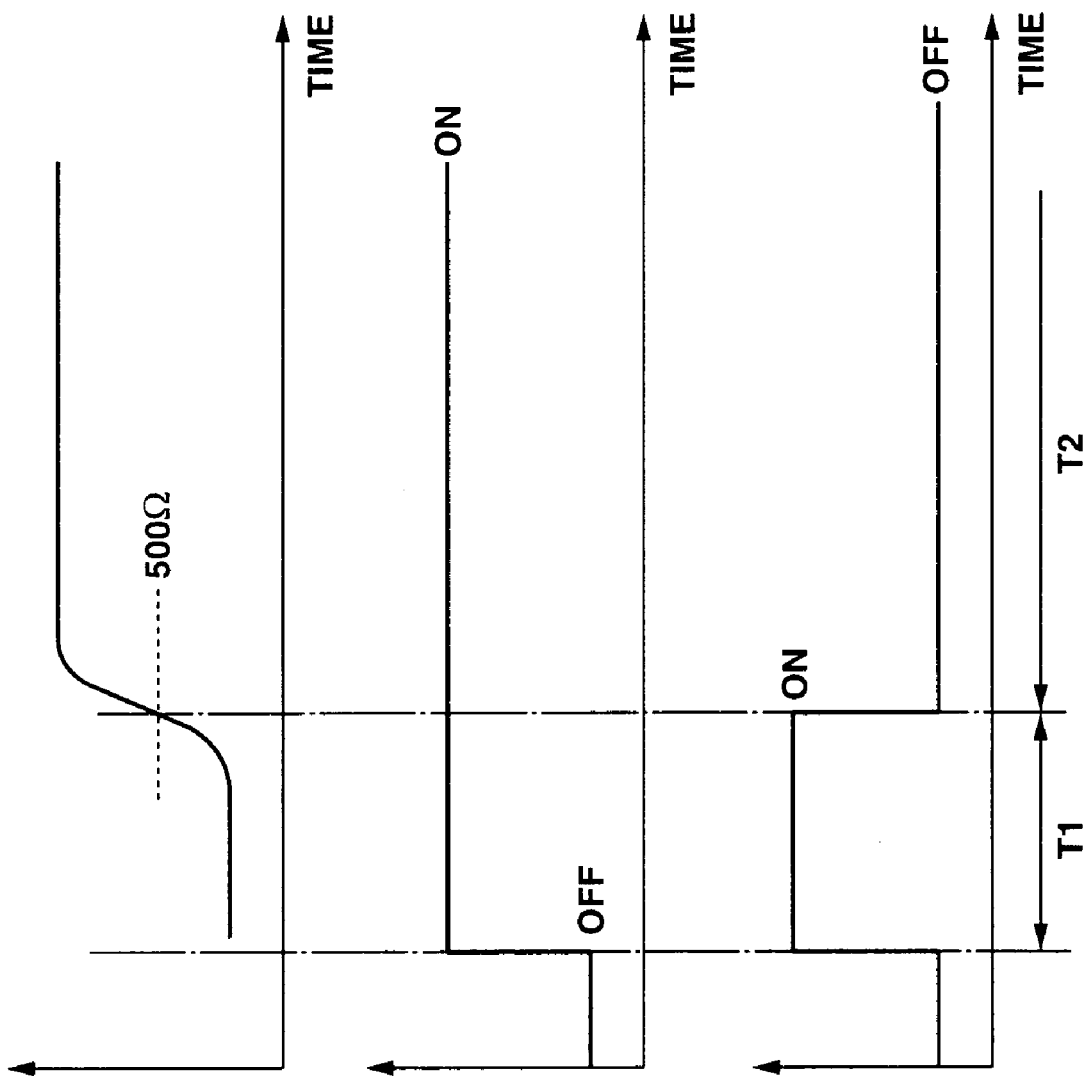
FIG. 42A is a timing chart showing how the resistance in the anatomy changes in the passage of time based on the flowchart shown in FIG. 41.
FIG. 42B is a timing chart showing the operation of a foot switch based on the flowchart shown in FIG. 41.
FIG. 42C is a timing chart showing an output characteristic of a heating power supply based on the flowchart shown in FIG. 41.

FIG. 41 is a flowchart showing the operation of the control circuit 226.

In step S71, the on/off pedal of the foot switch 212 is pressed. In step S72, the control circuit 226 operates the heating power supply 227 and flows current between two terminals of the active electrode 214. Thus, the physiological saline is heated near the active electrode 214 and the bubbles are easily generated. The bubbles are generated, then, the physiological saline is isolated from the active electrode 214, and the discharge operation easily starts.

In step S73, the control circuit 226 starts to output the high-frequency. In step S74, the control circuit 226 fetches the value of the current sensor 223 via the A/D converter 224.

In step S75, the control circuit 226 calculates impedance Z of the anatomy based on the current value obtained from the current sensor 223, thereby calculating the impedance between the active electrode 214 and the coating tube 215.

In step S76, the control circuit 226 detects the discharge operation by using the anatomy impedance (anatomy resistance).

Here, the anatomy impedance is lower than 500 Ω in the physiological saline before the start of discharge operation. On the other hand, the anatomy impedance is not less than 500 Ω after the start of discharge operation.

As a consequence, when the anatomy impedance is lower than 500 Ω (at timing T1 shown in FIGS. 42A to 42C), the control circuit 226 determines that the discharge operation does not start and repeats the similar processing in steps S74 to S76.

If the anatomy impedance is higher than 500 Ω (for a term T2 shown in FIGS. 42A to 42C), the discharge operation starts in the physiological saline.

Therefore, in step S77, the control circuit 226 stops the current output to the heating power supply 24 for supplying the heating current to the two terminals of the active electrodes 214 based on a relationship between the anatomy impedance and the output of the heating power supply shown in FIGS. 42A to 42C. Further, the control circuit 226 stops heating the physiological saline near the edge of the active electrode 214.

This is because that once the discharge operation starts, the discharge operation easily continues, and the physiological saline does not need to be heated near the active electrode 214.

In step S78, the on/off pedal of the foot switch 212 is off and, then, the control circuit 226 stops outputting the high-frequency in step S79.

When a coagulating pedal of the foot switch 212 is on and the coagulation set by a setting panel (not shown) of the high-frequency power supply 211 is not caused by the discharge operation, the control circuit 226 ignores steps S72 to S77.

On the contrary, when the coagulating pedal of the foot switch 212 is on and the coagulation set by the setting panel (not shown) of the high-frequency power supply 211 is caused by the discharge operation, the control circuit 226 performs steps S72 to S77, similarly to the operation of the on/off pedal.

Further, according to the seventh embodiment, not only the electrode shown in FIG. 38 but also the saw-blade-shaped and spiral-shaped active electrode 214 may be used as shown in FIGS. 39 and 40. In this case, the output current from the heating power supply 227 is consumed at the edge portion of the saw-blade-shaped and spiral-shaped active electrode 214. The edge portion of the active electrode 214 heats the physiological saline.

The operation timing of the control circuit 226 using the saw-blade-shaped and spiral-shaped active electrode 214 shown in FIG. 39 or 40 is the same as that using a loop electrode with high resistance.

According to the seventh embodiment, as mentioned above, after starting the output by the heating power supply 227, the physiological saline near the active electrode 214 is heated until the discharge operation starts. Therefore, according to the seventh embodiment, the bubbles are easily generated, the low power causes the bubbles to cover the entire active electrode 214, and the discharge operation starts. Then, the body anatomy is resected, is transpired, and is discharged and coagulated.

Further, according to the seventh embodiment, the discharge operation starts and then the current supply from the heating power supply 227 is stopped. Unnecessary power consumption is suppressed, and unnecessary heat is not applied to the body anatomy.

(Eighth Embodiment)

Figure 43:
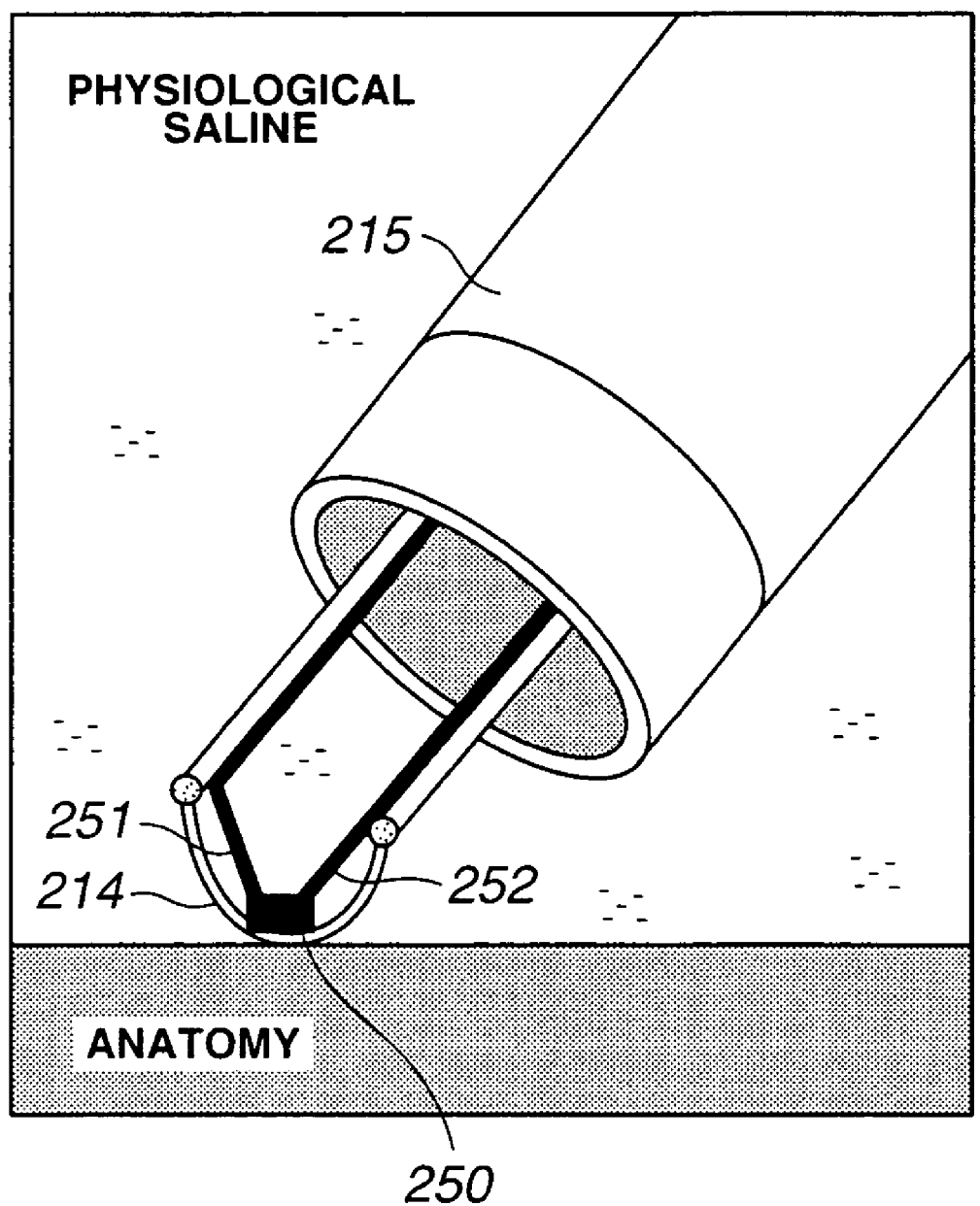
FIG. 43 is an enlarged view showing an edge of a resectoscope according to an eighth embodiment.

FIG. 43 is a diagram according to an eighth embodiment.

According to the eighth embodiment, the structure is almost the same as that according to the seventh embodiment. Therefore, only different points are described and the same components are designated by the same reference numerals. A description thereof is omitted.

Referring to FIG. 43, according to the eighth embodiment, a heating device 250 is attached to the edge of the active electrode 214. In the heating device 250, the heating power supply 227 outputs the heating current and then the current flows from a first conductor 51 for heating current to a second conductor 52 for heating current, thereby heating the active electrode 214. Other structures are the same as those according to the seventh embodiment.

Next, the operations with the above structure will be described according to the eighth embodiment.

The operation of the control circuit 226 using the active electrode 214 shown in FIG. 43 is almost the same as that in accordance with the flowchart shown in FIG. 41 according to the seventh embodiment.

However, when the high frequency is outputted in step S73 in FIG. 41, similarly to the case according to the seventh embodiment, the current flows to the heating device 250 and the physiological saline near the electrode is heated. Other operations are the same as those according to the seventh embodiment.

According to the eighth embodiment, as mentioned above, the heating efficiency is improved by using the heating device 250 and, after starting the output, the physiological saline near the active electrode 214 is heated until the discharge operation starts.

As a result, according to the eighth embodiment, the same advantages as those according to the seventh embodiment are obtained.

(Ninth Embodiment)

Figure 44:
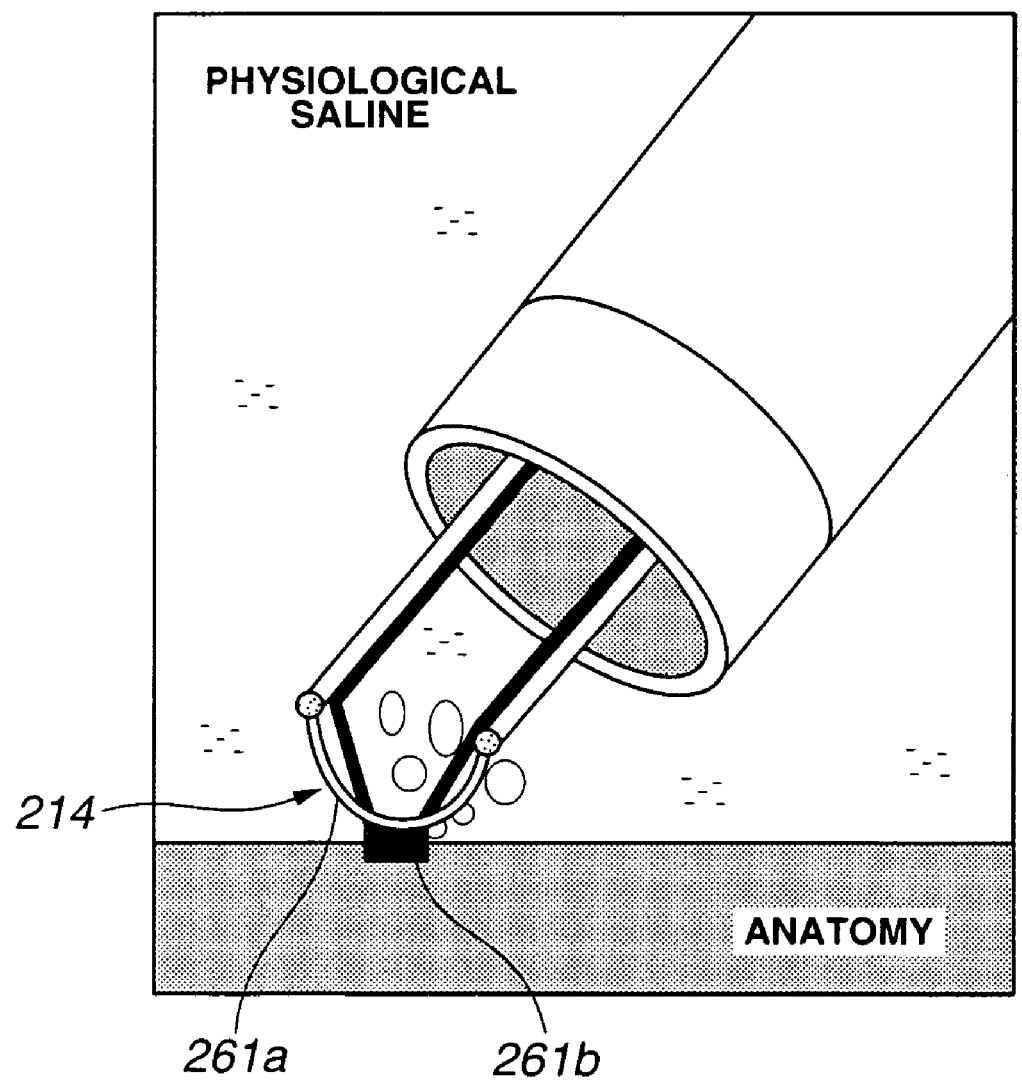
FIG. 44 is an enlarged view showing an edge of a resectoscope according to a ninth embodiment.
Figure 45:
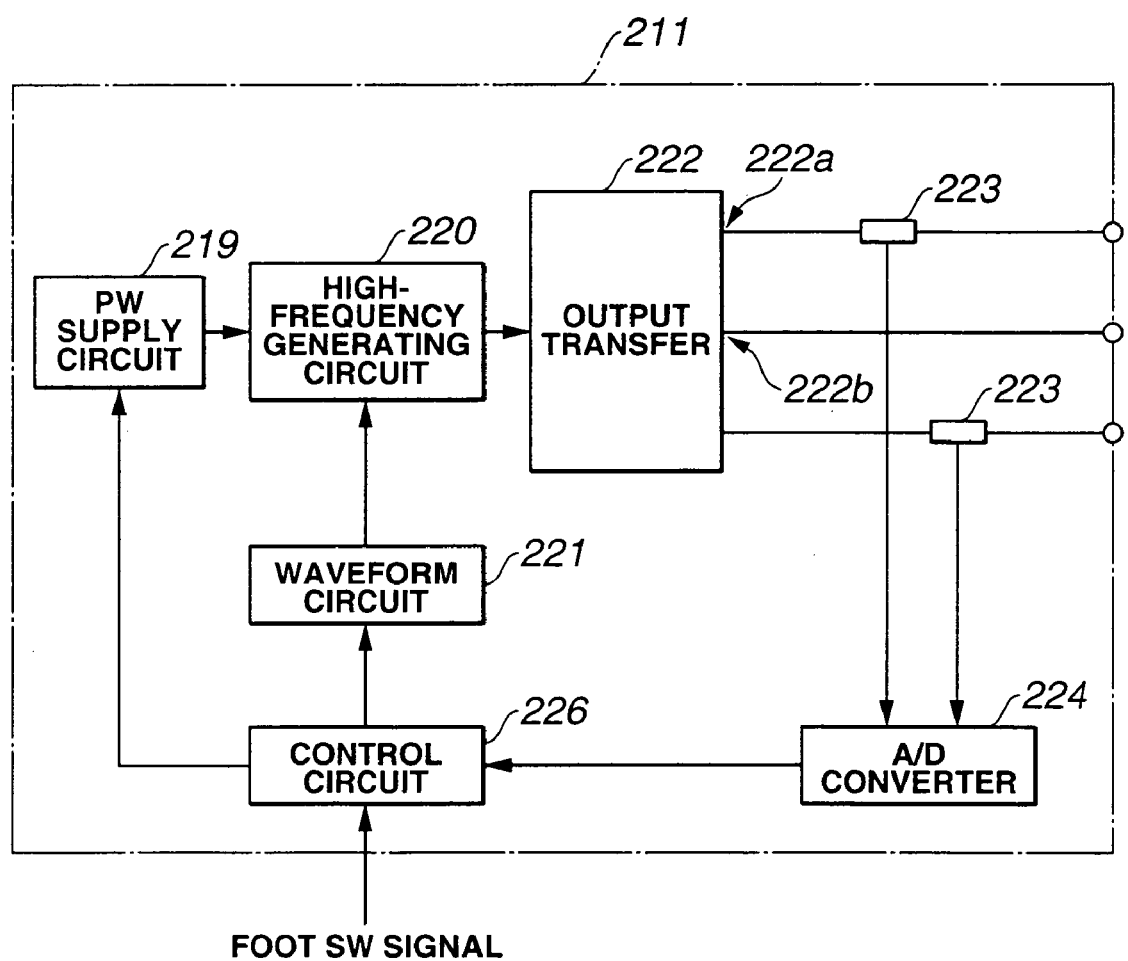
FIG. 45 is a circuitry block diagram showing a high-frequency power supply which outputs high-frequency current to an active electrode shown in FIG. 44.
Figure 46:
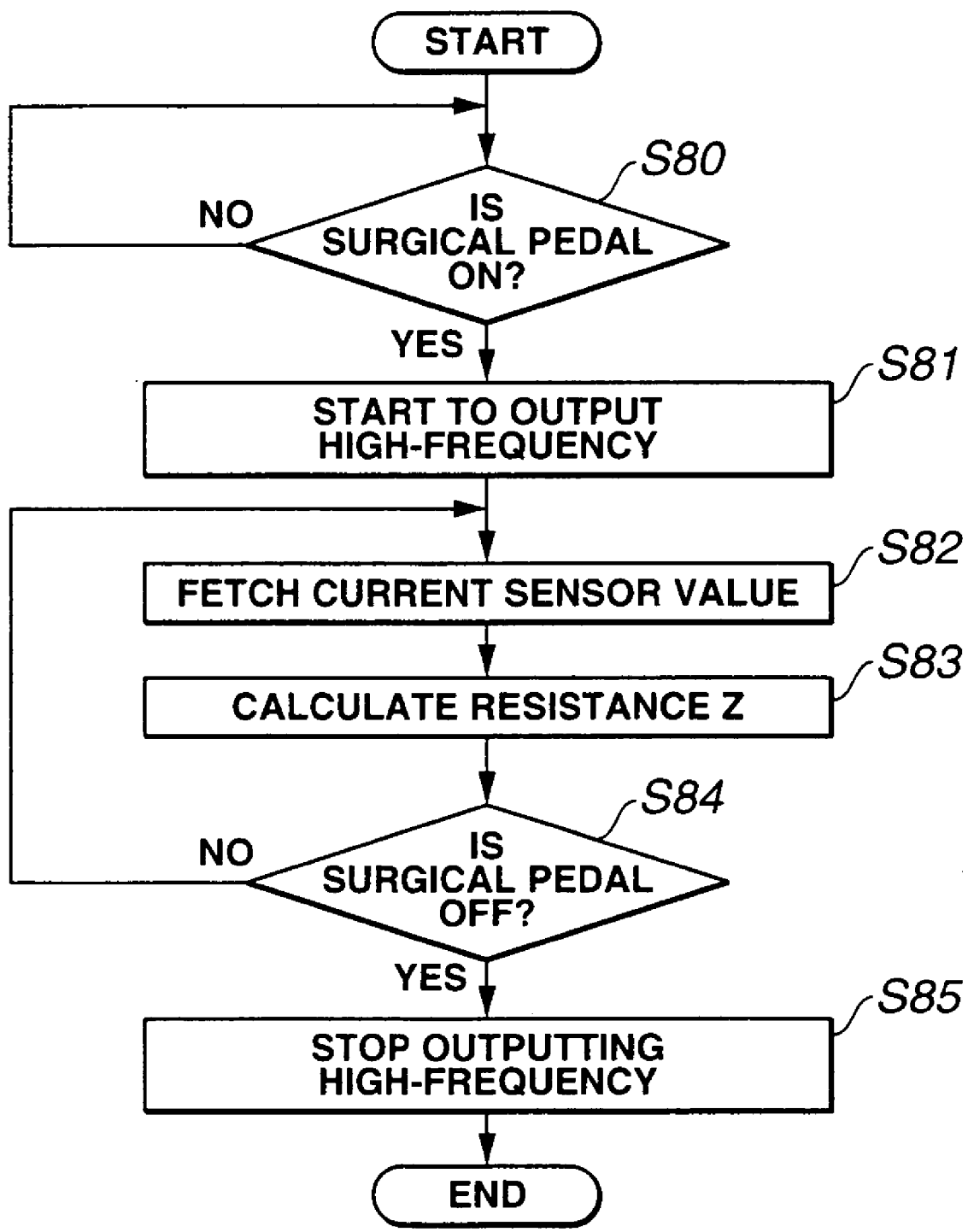
FIG. 46 is a flowchart showing the control operation of a control circuit according to the ninth embodiment.

FIGS. 44 to 46 are diagrams according to the ninth embodiment.

The structure according to the ninth embodiment are almost the same as that according to the seventh embodiment. Thus, only different points are descried, the same components are designated by the same reference numerals, and a description thereof is omitted.

Referring to FIG. 44, the active electrode 214 according to the ninth embodiment comprises two active electrodes of a first active electrode 261a for treatment of the anatomy having a large surface area and a second active electrode 261b for evaporating the physiological saline having a small surface area.

Referring to FIG. 45, according to the ninth embodiment, an output transfer 222 of the high-frequency power supply 211 comprises an output transfer portion 222a for outputting the high-frequency current from the high-frequency generating circuit 220 to the first active electrode 261a for treatment of the anatomy and an output transfer portion 222b for evaporating the physiological saline, for generating the bubbles near the first active electrode 261a, and for outputting the bubbles to the first active electrode 261a and the second active electrode 261b for isolating the physiological saline.

Other structure is the same as that according to the seventh embodiment.

Next, the operation with the above structure will be described according to the ninth embodiment.

The operation of the control circuit 226 is shown in a flowchart of FIG. 46 in the case of using the first active electrode 261a and the second active electrode 261b shown in FIG. 45.

That is, referring to FIG. 46, in step S80, the on/off pedal of the foot switch 212 is on. In step 81, the control circuit 226 outputs the high frequency. Then, the high-frequency current flows to the first active electrode 261a for anatomy treatment and the second active electrode 261b for evaporating the physiological saline.

Since the second active electrode 261b has a small contact area with the physiological saline, low power easily evaporates the physiological saline and the bubbles are generated.

The generated bubbles are collected near the first active electrode 261a, thereby isolating the first active electrode 261a from the physiological saline. The discharge operation is caused in the first active electrode 261a and then the treatment using the high frequency is possible.

In step S82, the control circuit 226 fetches the value of the current sensor 223 via the A/D converter 224.

In step S83, the control circuit 226 calculates the impedance Z of the anatomy based on the current value obtained from the current sensor 223, thereby calculating the impedance between the active electrode 214 and the coating tube 215. In step S84, the on/off pedal of the foot switch 212 is off and, in step S85, the control circuit 226 stops the output of high frequency.

As mentioned above, according to the ninth embodiment, the physiological saline is rapidly evaporated by using the two active electrodes and the discharge operation easily starts.

Further, according to the ninth embodiment, the two active electrodes 261a and 261b are connected to the high-frequency power supply 211, independently. Thus, the power does not change depending on the state of one of the two active electrodes 261a and 261b.

Furthermore, according to the ninth embodiment, since the high-frequency outputs transmitted to the two active electrodes 261a and 261b have the same phase, the potential difference between the active electrodes is not increased and the electrodes are not easily damaged.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electric operation apparatus comprising:
a high-frequency generating device which generates high-frequency current for treating the body anatomy;
an active electrode which supplies to adapted to supply the body anatomy with the high-frequency current generated by the high-frequency generating device;
a solution supply device which supplies a conductive solution around the active electrode;
a return electrode which returns, via the conductive solution supplied by the solution supply device, the high-frequency current supplied to the body anatomy from the active electrode in the conductive solution;
a sensor which detects a conductive state of the high-frequency current that flows between the active electrode and the return electrode;
a control device which determines a state of bubbles generated around the active electrode and which changes an operation mode, based on the conductive state of the high-frequency current detected by the sensor, the control device has a first operation mode for starting the discharge operation using the active electrode and a second operation mode for changing the conductive state of the high-frequency current after the start of discharge operation in the first operation mode; and
an air supply device which supplies air near the active electrode arranged in the conductive solution, the control device controlling the air supply device and changing the operation mode.

2. An electric operation apparatus according to claim 1, wherein the control device operates the air supply device in the first operation mode, and stops the operation of the air supply device in the second operation mode.

3. An electric operation apparatus according to claim 1, wherein the control device operates the air supply device after outputting the high-frequency current to the active electrode only when no discharge operation starts in the active electrode, and stops the air supply device when the discharge operation starts in the active electrode.

4. An electric operation apparatus comprising:
a high-frequency generating device which generates high-frequency current for treating the body anatomy;
an active electrode which supplies to adapted to supply the body anatomy with the high-frequency current generated by the high-frequency generating device;
a solution supply device which supplies a conductive solution around the active electrode;
a return electrode which returns, via the conductive solution supplied by the solution supply device, the high-frequency current supplied to the body anatomy from the active electrode in the conductive solution;
a sensor which detects a conductive state of the high-frequency current that flows between the active electrode and the return electrode;
a control device which determines a state of bubbles generated around the active electrode and which changes an operation mode, based on the conductive state of the high-frequency current detected by the sensor, the control device has a first operation mode for starting the discharge operation using the active electrode and a second operation mode for changing the conductive state of the high-frequency current after the start of discharge operation in the first operation mode; and
a heating power supply device which generates power for heating the active electrode arranged in the conductive solution, the control device controls the heating power supply device, and changes the operation mode,
wherein the high-frequency current is outputted to the active electrode, nearly simultaneously, the heating power supply device outputs DC or AC current to heat the active electrode and, upon detecting the start of discharge operation in the active electrode, nearly simultaneously, the control device stops the DC or AC current outputted from the heating power supply device.

5. An electric operation apparatus according to claim 4, wherein an edge portion of the active electrode is spiral-shaped or saw-blade-shaped.

6. An electric operation apparatus comprising:
a high-frequency generating device which generates high-frequency current for treating the body anatomy;
an active electrode which supplies to adapted to supply the body anatomy with the high-frequency current generated by the high-frequency generating device;

a solution supply device which supplies a conductive solution around the active electrode;
a return electrode which returns, via the conductive solution supplied by the solution supply device, the high-frequency current supplied to the body anatomy from the active electrode in the conductive solution;
a sensor which detects a conductive state of the high-frequency current that flows between the active electrode and the return electrode;
a control device which determines a state of bubbles generated around the active electrode and which changes an operation mode, based on the conductive state of the high-frequency current detected by the sensor, the control device has a first operation mode for starting the discharge operation using the active electrode and a second operation mode for changing the conductive state of the high-frequency current after the start of discharge operation in the first operation mode; and
an evaporation detecting portion which detects vapor of the conductive solution so as to detect the state of the bubbles near the active electrode, the control device changes the operation mode based on a detection result of the evaporation detecting portion,
wherein the control device operates the high-frequency generating device so that the peak of the high-frequency power or a crest factor of the high-frequency current is increased before detecting the evaporation of the conductive solution in the first operation mode, and operates the high-frequency generating device so that the peak of the high-frequency power or the crest factor of the high-frequency current is decreased after detecting the evaporation of the conductive solution in the second operation mode.

7. An electric operation apparatus comprising:
a high-frequency generating device which generates high-frequency current for treating the body anatomy;
an active electrode which supplies to adapted to supply the body anatomy with the high-frequency current generated by the high-frequency generating device;
a solution supply device which supplies a conductive solution around the active electrode;
a return electrode which returns, via the conductive solution supplied by the solution supply device, the high-frequency current supplied to the body anatomy from the active electrode in the conductive solution;
a sensor which detects a conductive state of the high-frequency current that flows between the active electrode and the return electrode;
a control device which determines a state of bubbles generated around the active electrode and which changes an operation mode, based on the conductive state of the high-frequency current detected by the sensor, the control device has a first operation mode for starting the discharge operation using the active electrode and a second operation mode for changing the conductive state of the high-frequency current after the start of discharge operation in the first operation mode; and
a promotion holding portion which promotes the generation of bubbles near the active electrode or holds the bubbles, the control device controlling the promotion holding portion, and changing the operation mode; the promotion holding portion being a solution supply stop portion which temporarily stops the solution supply of the conductive solution through the solution supply device, and the control device operates the solution supply stop portion in the second operation mode.

8. An electric operation apparatus comprising:
a high-frequency generating device which generates high-frequency current for treating the body anatomy;
an active electrode which supplies to adapted to supply the body anatomy with the high-frequency current generated by the high-frequency generating device;
a solution supply device which supplies a conductive solution around the active electrode;
a return electrode which returns, via the conductive solution supplied by the solution supply device, the high-frequency current supplied to the body anatomy from the active electrode in the conductive solution;
a sensor which detects a conductive state of the high-frequency current that flows between the active electrode and the return electrode;
a control device which determines a state of bubbles generated around the active electrode and which changes an operation mode, based on the conductive state of the high-frequency current detected by the sensor, the control device has a first operation mode for starting the discharge operation using the active electrode and a second operation mode for changing the conductive state of the high-frequency current after the start of discharge operation in the first operation mode; and
a discharge promoting portion which promotes the discharge operation in the active electrode, the control device controlling the discharge promoting portion, and changing the operation mode, the discharge promoting portion being an air supply device which supplies air near the active electrode arranged in the conductive solution.

* * * * *